US010042979B2

United States Patent
Moore et al.

(10) Patent No.: US 10,042,979 B2
(45) Date of Patent: Aug. 7, 2018

(54) SYSTEMS AND METHODS FOR INTEGRATING, UNIFYING AND DISPLAYING PATIENT DATA ACROSS HEALTHCARE CONTINUA

(71) Applicant: AirStrip IP Holdings, LLC, San Antonio, TX (US)

(72) Inventors: Stephen Trey Moore, San Antonio, TX (US); Augustine Vidal Pedraza, IV, San Antonio, TX (US); Neil R. McQueen, San Antonio, TX (US); Lloyd Kory Brown, San Antonio, TX (US); Thomas Scott Wade, Wimberley, TX (US); William Bryan Crane, San Antonio, TX (US); Jean-Francois Lancelot, San Diego, CA (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 512 days.

(21) Appl. No.: 14/193,560

(22) Filed: Feb. 28, 2014

(65) Prior Publication Data

US 2014/0249858 A1 Sep. 4, 2014

Related U.S. Application Data

(60) Provisional application No. 61/771,540, filed on Mar. 1, 2013.

(51) Int. Cl.
*G06F 19/00* (2018.01)
*G16H 10/60* (2018.01)

(52) U.S. Cl.
CPC ........... *G06F 19/322* (2013.01); *G16H 10/60* (2018.01)

(58) Field of Classification Search
CPC ........ G06Q 50/22; G06Q 50/24; G06Q 10/10; G06Q 40/08; G06Q 10/06; G06F 19/322;
(Continued)

(56) References Cited

U.S. PATENT DOCUMENTS 7,447,643 B1 * 11/2008 Olson ................. G06F 19/3418
434/236
7,509,264 B2 * 3/2009 Hasan ................... G06F 19/322
705/2

(Continued)

FOREIGN PATENT DOCUMENTS

WO WO2013158625 A1 10/2013
WO WO2013158632 A1 10/2013
WO WO2014134293 A1 9/2014

OTHER PUBLICATIONS

Authorized Officer Blaine R. Copenheaver, International Preliminary Report on Patentability International Application No. PCT/US2014/018987, dated Sep. 11, 2015, 7 pages.

(Continued)

*Primary Examiner* — Victoria P Shumate
*Assistant Examiner* — Gregory D. Moseley
(74) *Attorney, Agent, or Firm* — Fish & Richardson P.C.

(57) ABSTRACT

Implementations are directed to providing a user of a mobile device access to patient information and patient physiological data. Actions can include receiving user input, the user input indicating a user command to display a laboratory results screen for a particular patient, processing patient-specific data and lab results data to provide one or more tables, and displaying the laboratory results screen on the mobile device, the laboratory results screen including the one or more tables, each table of the one or more tables providing one or more discrete data values, wherein a
(Continued)

discrete data value of the one or more discrete values is user-selectable to provide detailed result information.

15 Claims, 27 Drawing Sheets
(20 of 27 Drawing Sheet(s) Filed in Color)

(58) Field of Classification Search
CPC ............. G06F 19/3418; G06F 19/3406; G06F 19/327; G06F 19/3487; G06F 19/345; G06F 19/3456; G06F 19/328; G06F 19/3481; A61B 5/0022; A61B 5/0002; A61B 5/0205; G16H 10/60
USPC .......................................................... 705/2, 3
See application file for complete search history.

(56) References Cited

U.S. PATENT DOCUMENTS

| | | | |
|---|---|---|---|
| 8,255,238 B2 | 8/2012 | Powell et al. | |
| 2003/0140044 A1 | 7/2003 | Mok et al. | |
| 2003/0204419 A1 | 10/2003 | Wilkes et al. | |
| 2004/0088317 A1 | 5/2004 | Fabrick et al. | |
| 2004/0172307 A1 | 9/2004 | Gruber | |
| 2004/0186746 A1 | 9/2004 | Angst et al. | |
| 2005/0015279 A1 | 1/2005 | Rucker | |
| 2005/0055242 A1 | 3/2005 | Bello et al. | |
| 2005/0149364 A1 | 7/2005 | Ombrellaro | |
| 2005/0159981 A1 | 7/2005 | Nagaeda et al. | |
| 2005/0228250 A1 | 10/2005 | Bitter et al. | |
| 2006/0004605 A1 | 1/2006 | Donoghue et al. | |
| 2006/0149597 A1 | 7/2006 | Powell et al. | |
| 2007/0094045 A1 | 4/2007 | Cobbs | |
| 2007/0203754 A1* | 8/2007 | Harrington ............ G06F 19/322 705/3 |
| 2008/0216060 A1* | 9/2008 | Vargas ...................... G06F 8/51 717/137 |
| 2009/0054743 A1 | 2/2009 | Stewart | |
| 2009/0216556 A1* | 8/2009 | Martin ................ G06F 19/3406 705/3 |
| 2009/0248437 A1 | 10/2009 | Gucciardi et al. | |
| 2010/0223071 A1* | 9/2010 | Kland ............... G06Q 10/06316 705/3 |
| 2010/0235728 A1 | 9/2010 | Hasuike | |
| 2010/0235782 A1 | 9/2010 | Powell et al. | |
| 2011/0054936 A1 | 3/2011 | Cowan et al. | |
| 2011/0138175 A1 | 6/2011 | Clark et al. | |
| 2011/0145012 A1 | 6/2011 | Nightingale et al. | |
| 2011/0178814 A1* | 7/2011 | McGlennen ........ G06F 19/3418 705/2 |
| 2011/0191124 A1 | 8/2011 | Sung et al. | |
| 2011/0246235 A1 | 10/2011 | Powell et al. | |
| 2011/0275940 A1 | 11/2011 | Nims et al. | |
| 2012/0046972 A1 | 2/2012 | Tonti et al. | |
| 2012/0173257 A1 | 7/2012 | Preiss et al. | |
| 2012/0226771 A1 | 9/2012 | Harrington et al. | |
| 2012/0296672 A1 | 11/2012 | Bates et al. | |
| 2013/0085771 A1 | 4/2013 | Ghanbari et al. | |
| 2013/0086201 A1 | 4/2013 | Legge | |
| 2013/0166317 A1 | 6/2013 | Beardall et al. | |
| 2013/0197679 A1* | 8/2013 | Balakrishnan .......... G06F 17/40 700/91 |
| 2013/0253339 A1 | 9/2013 | Reyes | |
| 2013/0304499 A1 | 11/2013 | Rangadass | |
| 2013/0304512 A1 | 11/2013 | Seshadri et al. | |
| 2014/0006058 A1 | 1/2014 | Schoenberg | |
| 2014/0032242 A1* | 1/2014 | LaBorde ............... G06F 19/322 705/3 |
| 2014/0095207 A1 | 4/2014 | Dhir et al. | |
| 2014/0122119 A1 | 5/2014 | Hardy | |
| 2014/0249854 A1 | 9/2014 | Moore et al. | |
| 2014/0249855 A1 | 9/2014 | Moore | |
| 2014/0249856 A1 | 9/2014 | Moore | |
| 2014/0249857 A1 | 9/2014 | Moore et al. | |
| 2014/0278486 A1 | 9/2014 | Moore et al. | |
| 2014/0278487 A1 | 9/2014 | Moore et al. | |
| 2014/0278488 A1 | 9/2014 | Moore | |
| 2015/0088549 A1 | 3/2015 | Moore et al. | |
| 2015/0254412 A1 | 9/2015 | Humphrys et al. | |
| 2015/0371176 A1 | 12/2015 | Barrett et al. | |
| 2017/0173262 A1 | 6/2017 | Veltz | |

OTHER PUBLICATIONS

Authorized Officer Blaine R. Copenheaver, International Search Report and Written Opinion for International Application No. PCT/US2014/018987, dated May 22, 2014, 8 pages.
European Search Report for Application No. 14756271.4, dated Aug. 8, 2016, 4 pages.
European Examination Report for Application No. 14756271.4, dated Aug. 23, 2016, 4 pages.
Google patents search, Jan. 9, 2017, 2 pages.
Director General F. A. Dos Santos, African Examination Report for Patent Application No. AP/P/2015/008727, dated Sep. 15, 2017, 4 pages.

* cited by examiner

SYSTEMS AND METHODS FOR INTEGRATING, UNIFYING AND DISPLAYING PATIENT DATA ACROSS HEALTHCARE CONTINUA

CROSS-REFERENCE TO RELATED APPLICATIONS

This application claims the benefit of and priority to U.S. Provisional Application No. 61/771,540 filed on Mar. 1, 2013, the disclosure of which is expressly incorporated herein by reference in the entirety.

BACKGROUND

Patient information can be stored across multiple facilities associated with respective health care providers. For example, healthcare continua can include hospitals, clinics, laboratories, and/or other healthcare facilities. In some instances, each healthcare facility had its own data source for storing patient information and data associated with services provided at the respective facility. For example, multiple, different electronic medical records (EMRs) can be provided for a particular patient across a healthcare continuum. In some examples, such EMRs are vendor-specific, storing data and information is disparate formats.

Physicians and other healthcare providers may be required to access patient data and information from across a healthcare continuum. The disparate nature, in which data and information may be stored, can complicate retrieval and display of relevant patient information to healthcare providers.

SUMMARY

Implementations of the present disclosure provide methods for providing a user of a mobile device access to patient information and patient physiological data. In some implementations, methods include actions of receiving user input, the user input indicating a user command to display a laboratory results screen for a particular patient, processing patient-specific data and lab results data to provide one or more tables, and displaying the laboratory results screen on the mobile device, the laboratory results screen including the one or more tables, each table of the one or more tables providing one or more discrete data values, wherein a discrete data value of the one or more discrete values is user-selectable to provide detailed result information. Other implementations of this aspect include corresponding systems, apparatus, and computer programs, configured to perform the actions of the methods, encoded on computer storage devices.

These and other implementations can each optionally include one or more of the following features: actions further include receiving, at the mobile device, the patient-specific data and the lab results data in response to the user input; the discrete data values are provided from the lab results data; the patient-specific data includes patient physiological data recorded from the particular patient; the lab results data includes lab results based on one or more samples taken from the particular patient; at least one discrete data value is color-coded; color-coding is based on a value range associated with a parameter represented by the at least one discrete data value; the discrete data value is color-coded based on a first color if the discrete data value is above the range, based on a second color if the discrete value is within the range, and based on a third color if the discrete value is below the range; at least one discrete data value is annotated; an annotation associated with the discrete data value indicates one of a decrease, a significant decrease, an increase and a significant increase in the discrete data value relative to another discrete data value; a warning annotation is associated with the discrete data value; actions further include receiving a user-selection associated with a discrete data value and, in response, displaying a window, the window displaying detailed information associated with the discrete data value; and wherein the detailed information includes at least one of a name of a laboratory that generated the discrete data value, collection information associated with collection of a specimen of the particular patient, textual comments, and laboratory contact information.

Other aspects of the present disclosure provide systems including one or more processors, and a computer-readable medium coupled to the one or more processors having instructions stored thereon which, when executed by the one or more processors, cause the one or more processors to perform one or more of the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more implementations are set forth in the accompanying drawings and the description below. Other features, objects, and advantages will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Like reference symbols in the various drawings indicate like elements.

DETAILED DESCRIPTION

Implementations of the present disclosure are generally directed to an enterprise scalable, data- and vendor-agnostic mobility architecture to securely deliver patient data and information from medical devices, electronic medical records (EMRs) and patient monitors to healthcare providers anywhere across a healthcare continuum. More particularly, implementations of the present disclosure provide integrated and unified views of patient data and patient information on mobile devices (e.g., smartphones, tablets) from a plurality of data sources across the healthcare continuum. As discussed in further detail herein, implementations of the present disclosure enable timely and collaborative clinical decision-making, and enable healthcare systems to better track quality metrics, empower a mobile workforce, expand networks, and achieve clinical transformation.

Figure 1:
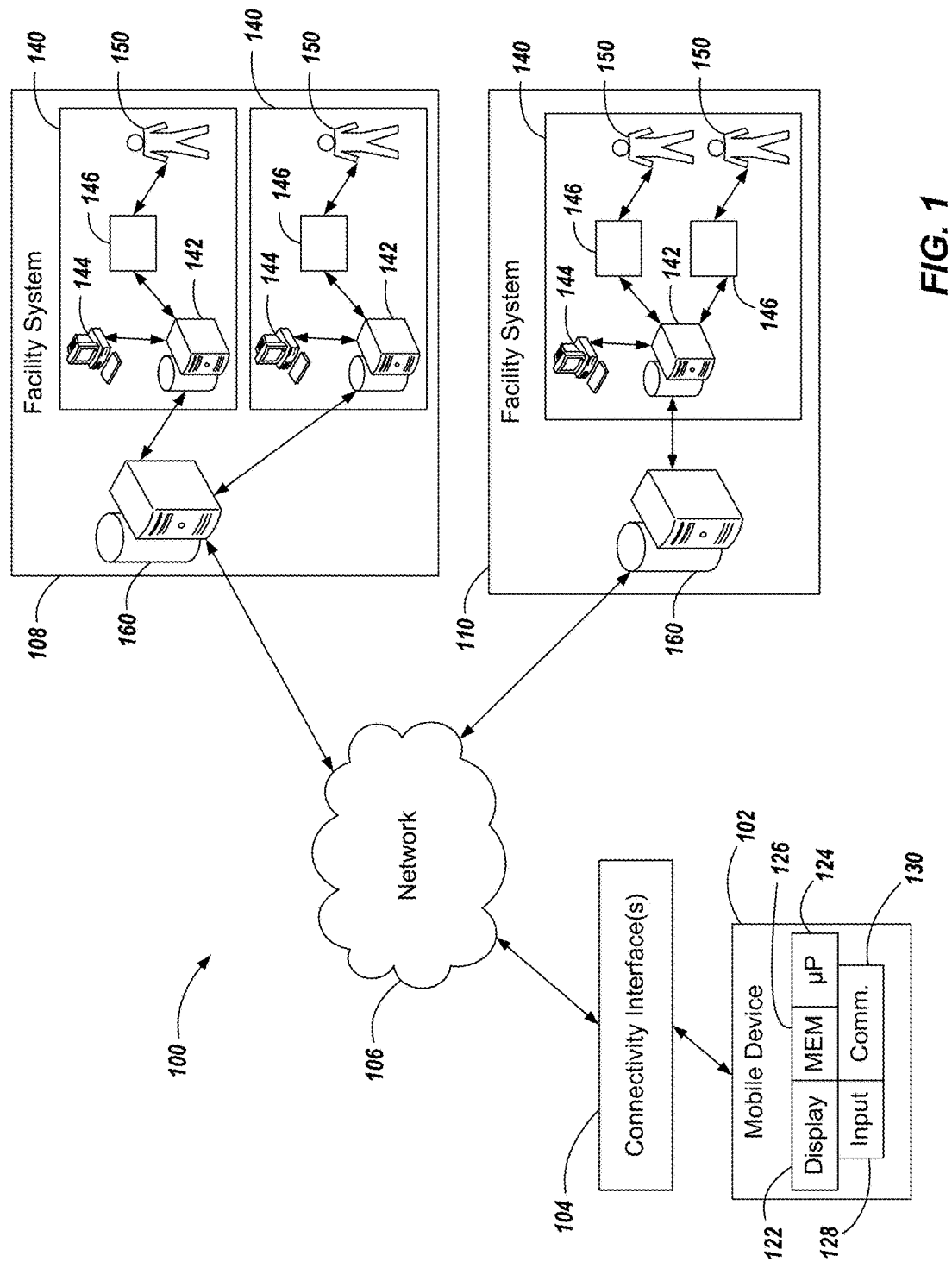
FIG. 1 is a schematic illustration of an example system architecture in accordance with implementations of the present disclosure.

Referring now to FIG. 1, an example system architecture 100 is illustrated, and includes a mobile device 102, connectivity interface(s) 104, a network 106, a first facility system 108, and a second facility system 110. As discussed in further detail herein, data is transferred from each of the first and second facility systems 108, 110 through the network 106 and connectivity interface(s) 104 for presentation, or display on the mobile device 102. Further, data can be transferred from the mobile device 102 through the connectivity interface(s) 104 and the network 106 to each of the first and second facility systems 108, 110. Although a single mobile device 102 is illustrated, it is contemplated that one or more mobile devices 102 can communicate with each of the first and second facility systems 108, 110 through the network 106 and the connectivity interface(s) 104. Similarly, although two facility systems are illustrated, implementations of the present disclosure can include one or more facility systems.

The mobile device 102 can include any number of example devices. Such example devices include, but are not limited to, a mobile phone, a smartphone, a tablet computing device, a personal digital assistant (PDA), a laptop personal computer (PC), a desktop PC, and/or appropriate combinations thereof. In the depicted example, the mobile device 102 includes a display 122, a processor 124, memory 126, an input interface 128, and a communication interface 130. The processor 124 can process instructions for execution of implementations of the present disclosure. The instructions can include, but are not limited to, instructions stored in the memory 126 to display graphical information on the display 122. Example displays include, but are not limited to, a thin-film-transistor (TFT) liquid crystal display (LCD), or an organic light emitting diode (OLED) display. The memory 126 stores information within the mobile device 102. In some implementations, the memory 126 can include a volatile memory unit or units, and/or a non-volatile memory unit or units. In other implementations, removable memory can be provided, and can include, but is not limited to, a memory card. Example memory cards can include, but are not limited to, a secure digital (SD) memory card, a mini-SD memory card, a USB stick, and the like.

In some examples, the input interface 128 can include a keyboard, a touchscreen, a mouse, a trackball, a microphone, a touchpad, and/or appropriate combinations thereof. In some implementations, an audio codec (not shown) can be provided, which receives audible input from a user or other source through a microphone, and converts the audible input to usable digital information. The audio codec can generate audible sound, such as through a speaker that is provided with the mobile device 102. Example sounds can include sound from voice telephone calls, recorded sound (e.g., voice messages, music files, etc.), and/or sound generated by applications operating on the mobile device 102.

The mobile device 102 may communicate wirelessly through the communication interface(s) 104, which can include digital signal processing circuitry. The communication interface(s) 104 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the mobile device can be capable of short-range communication using features including, but not limited to, Bluetooth and/or WiFi transceivers (not shown).

The mobile device 102 communicates with the network 106 through the connectivity interface(s) 104. In some examples, the connectivity interface(s) 104 can include a satellite receiver, cellular network, a Bluetooth system, a Wi-Fi system (e.g., 802.x), a cable modem, a DSL/dial-up interface, a private branch exchange (PBX) system, and/or appropriate combinations thereof. Each of these connectivity interfaces 104 enables data to be transmitted to/from the network 106. In some examples, the network 106 can be provided as a local area network (LAN), a wide area network (WAN), a wireless LAN (WLAN), a metropolitan area network (MAN), a personal area network (PAN), the Internet, and/or combinations thereof.

Figure 2:
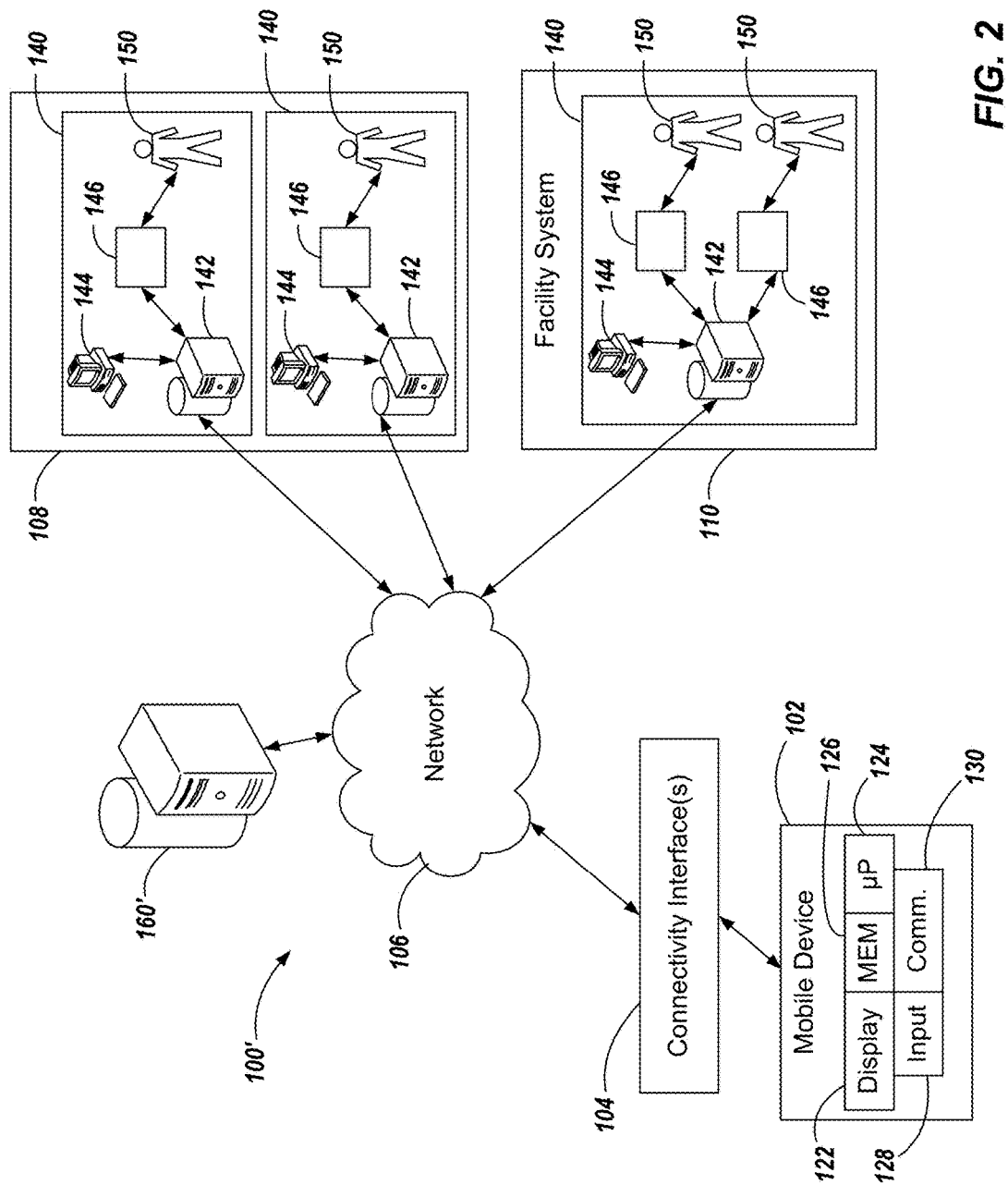
FIG. 2 is a schematic illustration of another example system architecture in accordance with implementations of the present disclosure.

In the example systems of FIGS. 1 and 2, the first facility system 108 includes a plurality of facilities 140, and the second facility system 110 includes a facility 140. It is contemplated that each facility system 108, 110 can include one or more facilities, and is not limited to the example arrangement described herein. In the case of multiple facilities, the facilities can be remotely located from one another, and/or can be located at a common location, or site (e.g., separate departments in a common (the same) building). Each facility system 108, 110 can be provided as a medical care system, for example, which medical care system can include one or more hospitals, hospital systems, clinics, physician offices, and the like.

In some examples, each facility 140 includes an associated information system 142, computer interface(s) 144, and patient monitoring device(s) 146. Example information systems can include, but are not limited to, a clinical information system (CIS), an EMR system, an electronic health record (EHR) system, and/or a hospital information system (HIS). Each information system 142 can be provided as a server, and supports the acquisition, storage, modification, and distribution of clinical information, such as patient data, throughout the facility 140 and/or facility system 108, 110. In some examples, each information system 142 can communicate with one or more ancillary information systems (not shown) that can include, but are not limited to, a pharmacy management system, a laboratory management system, and/or a radiology management system. Although the example system architecture 100 includes an information system 142 located at each facility 140, it is contemplated that the facilities 140 can communicate with a common information system 142 that is remotely located from either facility 140, or that is located at one of the facilities 140 within the facility system 108, 110.

In some examples, the computer interface 144 can communicate with the information system 142 to enable access to information that is stored within, and managed by the information system 142. In some examples, the computer interface 144 can include a personal computer (PC) (e.g., desktop, laptop, or tablet). Although a single computer interface 144 is illustrated in the example architectures described herein, it is contemplated that one or more computer interfaces 144 can communicate with the information system 142. Communication between each computer interface 144 and the information system 142 can be achieved via a direct connection, or remotely through a network (not shown) that can include, but is not limited to, a LAN, a WAN, a WLAN, and/or the Internet.

In some examples, each patient monitoring device 146 monitors physiological characteristics of a particular patient 150, and generates data signals based thereon. As discussed in further detail herein, implementations of the present disclosure provide patient monitoring devices that include a computing device, such as a tablet computing device. The data signals are communicated to the information system 142, which collects patient data based thereon, and stores the data to a patient record that is associated with the particular patient. An example patient record can include an electronic medical record (EMR). Although a single patient monitoring device 146 is illustrated per each patient 150, it is contemplated that multiple patient monitoring devices 146 can monitor a particular patient 150. The patient monitoring device(s) 146 can communicate with the information system 142 via a direct connection, or remotely through a network (not shown) that can include, for example, a LAN, a WAN, a WLAN, and/or the Internet.

In some examples, the patient data is made available for display on the computer device 144. A healthcare provider (e.g., a nurse and/or physician) can augment the patient data by inputting patient information that is also stored to the information system 144. More specifically, the healthcare provider can input patient information corresponding to a particular patient 150, which patient information can be stored to the patient record (e.g., EMR). As one example, a nurse can input nursing notes, which nursing notes can be stored to the patient record in the information system. Example patient information can include any non-physiological information corresponding to a patient (e.g., name, age, date-of-birth (DOB), gender).

As discussed above, each information system 142 stores patient data that can be collected from the patient monitoring devices 146, as well as additional patient information, that can include information that is input by a healthcare provider. The information system 144 communicates the patient data and/or the additional patient data to a data management system (DMS) 160. The DMS 160 can be provided as a server, or a virtual server, that runs server software components, and can include data storage including, for example, a database and/or flat files. In the example system architecture 100 of FIG. 1, each facility system 108, 110 includes a corresponding DMS 160. In such an arrangement, each information system 142 communicates patient data, and/or additional patient data to the DMS 160. Furthermore, and as discussed in further detail below, the DMS 160 can communicate ancillary information to the information system 142. Communication between the DMS 160 and the information system(s) 142 can be achieved via a direct connection, or remotely through a network (not shown) that can include, for example, a LAN, a WAN, a WLAN, and/or the Internet.

In some examples, a DMS 160 corresponding to a particular facility system can be remotely located from any of the facilities 140 of the facility system 108, 110, or can be located at a particular facility 140 of the facility system 108, 110. In the example system architecture 100 of FIG. 1, the DMS 160 is remotely located from either facility 140 within each of the facility systems 108, 110. It is contemplated, however, that the DMS 160 can be located at one of the facilities 140, and remote from the other facility 140.

In the example system architecture 100' of FIG. 2, a DMS 160' is provided that is common to (the same for) the facility systems 108, 110. For example, the DMS 160' can be described as being common to various facility systems 108, 110, and is not associated with a particular facility system 108, 110. For example, the DMS 160' can be hosted by a third-party vendor (e.g., a cloud service provider). In some examples, each information system 42 communicates with the DMS 160' via a direct connection, or remotely through a network (not shown) that can include, but is not limited to, a LAN, a WAN, a WLAN, and/or the Internet. In the example arrangement of FIG. 2, the DMS 160' communicates with each of the information systems 142 through the network 106. The information systems 142 communicate patient data and/or patient information to the DMS 160', and the DMS 160' can communicate ancillary information to the information system 142, as discussed in further detail below.

In the example system architecture 100 of FIG. 1, the facility 140, or facility system 108, 110 installs the DMS 160 as a local DMS, and the DMS 160 sits at the local site with other servers that can include, for example, the information system 142. In some implementations, the DMS 160 can be sectioned off, or separated from a logical network perspective, but still physically exists with the other servers that belong to the respective facility 140. In some examples, server components are installed on the DMS 160, which components can include, for example, a database component, a database synchronization component, a web services component, and/or a structured query language (SQL) component. An information system interface can also be installed on the DMS 160, and functions as the interface to the information system 142. As one example, the information system interface can include OBLink, provided by GE Healthcare. In some implementations, the DMS 160 can be arranged in a multiple server configuration, in which one server only hosts web service related components and is logically segregated, and another server has the remaining necessary server components installed.

The example system architecture 100' of FIG. 2, provides for the remote location of data collection at the DMS 160'. In such implementations, the DMS 160' can be provided at a third-party site, remote from any of the facilities 140, or facility systems 108, 110. The third-party functions as a DMS host, and the necessary server components are installed on the remotely hosted DMS 160'. In some implementations, a business-to-business (B2B) virtual private network (VPN) can be created between the remotely hosted DMS 160' and the network of the facility 140 or facility system 108, 110. In this manner, the facility 140 and/or facility system 108, 110 forgoes the purchase and/or maintenance of another physical server, or DMS 160. Further, the up-time and the status of availability of the DMS 160' are easier to manage on the part of a dedicated third-party. The DMS' access to the network can be attended to by the third-party, as opposed to burdening the facility 140, or the facility systems 108, 110. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

In accordance with implementations of the present disclosure, the DMS 160, 160' synchronizes and transfers data between the mobile device 102, or multiple mobile devices 102, and the information system 142, or multiple information systems 142. More specifically, the DMS 160, 160' processes and prepares the patient data and/or patient information for transfer to and presentation on the mobile device 102, or multiple mobile devices 102, from the information system 142, and/or other systems, as discussed in further detail herein. The DMS 160, 160' also processes and prepares ancillary information for transfer to and storage in the information system 142 from the mobile device 102, or multiple mobile devices 102 for potential presentation at a corresponding computer device 144. Example DMSs can include, but are not limited to, the AirStrip Server provided by AirStrip Technologies, LLC, which AirStrip Server includes AirStrip Server Components installed therein.

Figure 3:
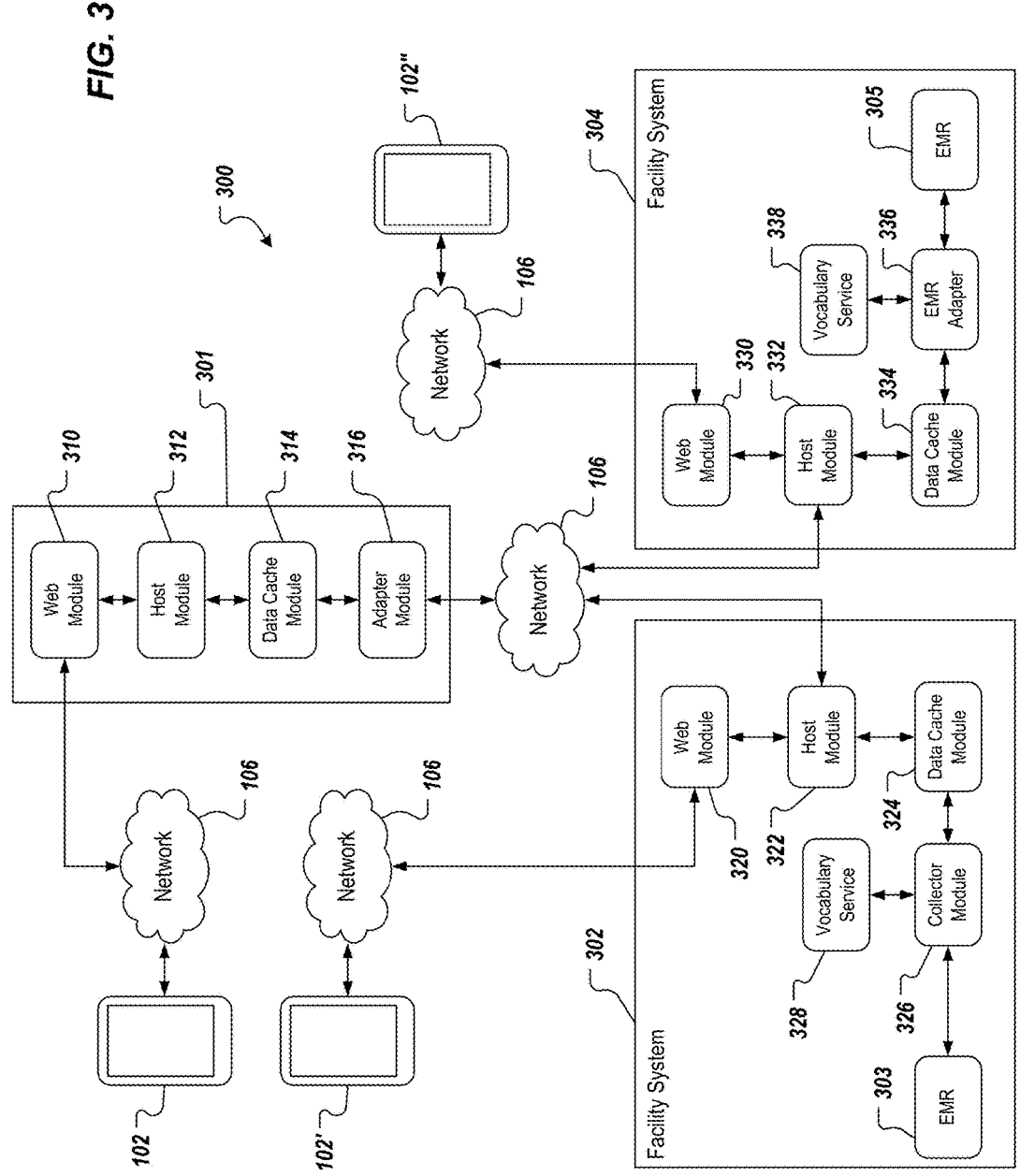
FIG. 3 is a functional block diagram of an example system in accordance with implementations of the present disclosure.
Figure 4:
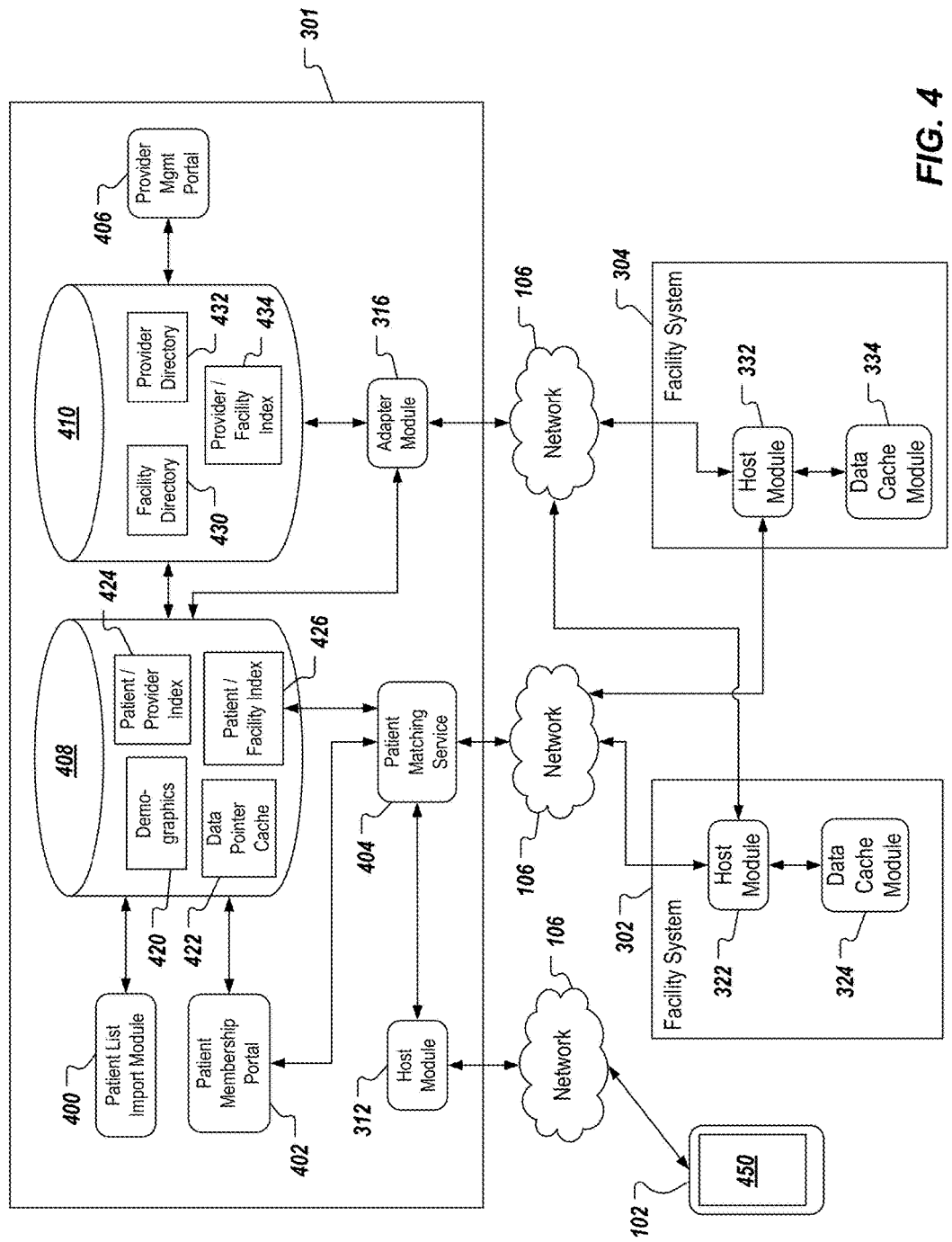
FIG. 4 is a more detailed view of the functional block diagram of FIG. 3.

Referring now to FIGS. 3 and 4, example module structure, or system 300 that can be implemented to provide features of the present disclosure will be described in detail. In some examples, the example system 300 enables patient data and patient information to be communicated to/from, and to be exchanged between mobile devices and data sources across healthcare continua. In some examples, each module can be provided as one or more computer-executable programs that are executed using one or more computing devices (e.g., computing devices provided as part of a DMS, computing devices located at one or more facilities of a facility system).

FIG. 3 illustrates an overview of the example system 300. In the depicted example, the module structure includes modules located at a DMS 301, a first facility system 302 and a second facility system 304. In some examples, the first facility system 302 and the second facility 304 can be included in at least a portion of a healthcare continuum, discussed in further detail herein. The facility system 302 includes a patient record module 303 (e.g., EMR module) that accesses one or more patient records managed and stored by the facility system 302. The facility system 304 includes a patient record module 305 (e.g., EMR module) that accesses one or more patient records managed and stored by the facility system 304.

In the depicted example, and as discussed in further detail herein, patient data and/or information can be provided for integrated and unified display on the mobile device 102 through the network 106 and the DMS 301 from across healthcare continua (e.g., the facility systems 302, 304). In some examples, patient data and/or information can be provided for display on a mobile device 102', 102" through the network 106 from a facility system (e.g., the facility system 302, 304). In some examples, the mobile devices 102, 102', 102" are the same device. That is, for example, a mobile device can receive patient data and/or information from across a healthcare continuum, and/or from individual facility systems.

In some implementations, the DMS 301 includes a web module 310, a host module 312, a data cache module 314 and an adapter module 316, web module 320, a host module 322, a data cache module 324, a collector module 326. In general, modules of the DMS 301 enable the DMS 301 to retrieve and combine data from multiple facility systems (e.g., the facility systems 302, 304) across healthcare continua. In some examples, the web module 310 provides a first-level network facing interface to the DMS infrastructure. In some examples, and in response to a request from a mobile device (e.g., the mobile device 102), the web module 310 performs request validation and user authentication and routes the request to the host module 312. In some examples, the web module 310 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some implementations, the host module 312 orchestrates request processing. In some examples, the host module 312 includes one or more sub-modules. Example sub-modules include a request parsing sub-module that parses received requests, a pipeline assembly sub-module, a pipeline processing sub-module, an operation execution sub-module, a data access sub-module, a results formatting sub-module, an access control sub-module, an encryption sub-module, a data conditioning sub-module, and a logging sub-module. In some examples, the host module 312 parses a received request (e.g., using the request parsing sub-module) to determine, for example, what type of device issued the request, which application executing on the device issued the request, and/or patient data/information (or other data such as analytical data, discussed below) is needed to fulfill the request. In some examples, and based on the parsed information, the host module 312 builds a pipeline (e.g., using the pipeline assembly sub-module). In some examples, a pipeline can be provided as a list of tasks that need to be executed to fulfill the request. Example tasks can include retrieving particular patient data/information, processing retrieved patient data to generate additional data and/or data visualizations (e.g., analytical data, trend graphs, discussed below), encrypting/decrypting retrieved data, performing access control to retrieve data, generating logs of tasks.

In some implementations, the host module 312 coordinates data retrieval with the data cache module 314 (e.g., using the data access sub-module). The retrieved data is provided back to the host module 312. In some examples, the host module 312 processes the retrieved data (e.g., using the operation execution sub-module, the results formatting sub-module and/or the data conditioning sub-module). In some examples, the retrieved data is processed to generate additional data (e.g., data used for data visualizations). In some examples, the retrieved data and/or the additional data are conditioned to provide efficient transfer back to the requesting mobile device. In some examples, conditioning can include converting data based on transmission protocol, formatting data for optimal display on the particular device, and/or packaging data to send to the requesting device.

In some implementations, the data cache module 314 enables access to and optional storage of detailed patient data/information used by other components of the system 300. In some examples, the data cache module 314 includes one or more sub-modules and/or data stores. An example sub-module can include a cache services sub-module. In some examples, the data cache module 314 can operate in a pass-through mode (real-time mode) and a reposed mode. In some examples, patient data/information required to satisfy a given request can be directly accessed from a source system (e.g., the facility system 302, 304) in real-time. In such examples, the data cache module 314 operates in a pass-through mode, retrieving the patient data/information from multiple data sources and passing the patient data/information onward for responding to the request. In some examples, an application program interface (API), or other programmatic mechanism can be used to retrieve the patient data/information. In some examples, in the pass-through mode, patient data/information is not stored in a persistent data store accessed by the data cache module 314. In some implementations, it might be desired to improve retrieval performance. Consequently, the data cache module 314 can store data identifiers and/or pointers in a persistent data store. When in the pass-through mode, the data cache module 314 uses the adapter module 316 to perform the actual retrieval of patient data/information from one or more facility systems.

In some examples, the patient data/information that is required to satisfy a request cannot be directly accessed from the facility systems (e.g., the facility systems 302, 304). In such examples, the data cache module 314 operates in the reposed mode. In some examples, in the reposed mode, the data cache module 314 stores a detailed copy of the patient data/information in the persistent data store. That is, for example, stored patient data/information is stored at the DMS-level, but had been retrieved from remote data sources (e.g., data sources located at the facility systems 302, 304). In some examples, when a request is made for patient data/information in the reposed mode, the patient data/information is retrieved directly from the persistent data store (e.g., by the cache services sub-module).

In some implementations, the adapter module 316 enables the retrieval of patient data/information from across healthcare continua. Consequently, the adapter module 316 can be referred to as a federated adapter module. In some examples, in response to receiving a request from the mobile device 102 for patient data/information from multiple data sources (e.g., the facility systems 302, 304), the data cache module 314 utilizes the adapter module 316 to retrieve the requested patient data/information from the multiple data sources. In some examples, the adapter module 316 communicates with local host modules (discussed in further detail below) of the respective facility systems.

In some implementations, the request processing operation of the DMS 301 is stateless. More particularly, the modules of the DMS 301 handle each received request as a distinct unit and, once a request is handled, stores no state information associated with a completed request. In other words, after the DMS 301 has processed a request, the DMS 301 (e.g., modules within the DMS 302 that handled the request) "forget" that the request even occurred. In this manner, subsequently received requests are not influenced by (e.g., handled based on) previously processed requests.

In some examples, operation of the DMS 301 is stateless, but the DMS 301 can still provide a log of requests handled (e.g., using the logging sub-module). For example, a request log can be accessed during an audit of the system 300.

In some implementations, each facility system 302, 304 includes one or more local web modules 320, 330, one or more local host modules 322, 332, one or more local data cache modules 324, 334, and one or more vocabulary service modules 328, 338. In the depicted example, the facility system 302 includes one or more collector modules 326, and the facility system 304 includes one or more patient record (EMR) adapter modules 336.

In some examples, each of the web modules 320, 330 provides functionality as similarly discussed above with respect to the web module 310. More particularly, the web modules 320, 330 operate at a local level (e.g., local to the respective facility systems 302, 304), each performing request validation and user authentication, and routing requests to the respective local host modules 322, 332. For example, the web modules 320, 330 can receive requests from the respective mobile devices 102', 102", can validate the requests and authenticate the respective users/mobile devices, and route the requests accordingly. In some examples, each web module 320, 330 includes one or more sub-modules. Example sub-modules include a request validation sub-module, which validates received requests, a user authentication module, which authenticates an identity of the user and/or mobile device from which a request is received, and a request routing sub-module, which routes requests after validation and authentication.

In some examples, each of the local host modules 322, 332 provides functionality as similarly discussed above with respect to the host module 312. More particularly, the local host modules 322, 332 operate at a local level (e.g., local to the respective facility systems 302, 304), each orchestrating request processing. In some examples, the local host modules 322, 332 orchestrate request processing for requests received from the mobile device 102 through the DMS 301, and/or from the respective mobile devices 102', 102" through the respective local web modules 320, 330. In some examples, each local host module 322, 332 includes one or more sub-modules. Example sub-modules include a request parsing sub-module that parses received requests, a pipeline assembly sub-module, a pipeline processing sub-module, an operation execution sub-module, a data access sub-module, an access control sub-module and an encryption sub-module.

In some examples, each of the local data cache modules 324, 334 provides functionality as similarly discussed above with respect to the data cache module 314. More particularly, the local data cache modules 324, 334 operate at a local level (e.g., local to the respective facility systems 302, 304), each enabling access to and optional storage of detailed patient data/information used by other components of the system 300. In some examples, the each data cache module 324, 334 can operate in a pass-through mode and a reposed mode, as discussed above with respect to the data cache module 314. In the pass-through mode, the local data cache modules 324, 334 retrieve the patient data/information from one or more local data sources and passed the patient data/information onward for responding to the request. In some examples, it might be desired to improve retrieval performance. Consequently, the local data cache modules 324, 334 can store data identifiers and/or pointers in a persistent data store. When in the pass-through mode, the local data cache modules 324, 334 use the collector module 326 and the patient record adapter module 336, respectively, to perform the actual retrieval of patient data/information from local data source(s) (e.g., the patient record module 303 and the patient record module 305, respectively). In some examples, when in the pass-through mode, the local data cache modules 324, 334 can write data back to the respective patient record modules 303, 305.

In some examples, the patient data/information that is required to satisfy a request (e.g., from the mobile device 102', 102") cannot be directly accessed from the local data sources (e.g., the patient record modules 303, 305). In such examples, each local data cache module 324, 334 can operate in the reposed mode. In some examples, in the reposed mode, the local data cache module 324, 334 stores a detailed copy of the patient data/information in the persistent data store. That is, for example, stored patient data/information is stored at the local level, having been previously received from local data source(s) (e.g., the patient record modules 303, 305). In some examples, when a request is made for patient data/information in the reposed mode, the patient data/information is retrieved directly from the persistent data store (e.g., by the cache services sub-module).

In some implementations, the collector module 326 and the adapter module 336 are specific to the type of patient record module 303, 305, respectively. In the example of FIG. 3, the patient record module 303 can be accessed based on a particular messaging protocol. An example messaging protocol can include the Health Level 7 (HL7) messaging protocol. In some examples, patient data/information provided based on such messaging protocols is reposed by the data cache module 324. Consequently, requests for such data can be fulfilled based on operation of the data cache module 314 and/or the local data cache module 324 in the reposed mode, as discussed above. In some examples, changes to patient records in the patient record module 303 can trigger updating of reposed patient data/information by the data cache modules 314, 324. For example, the collector module 326 can automatically receive a message from the patient record module 303 in response to a change/updated, triggering updating/changing of reposed patient data/information.

In the example of FIG. 3, the patient record module 305 supports programmatic interface (e.g., API) access. In some examples, patient data/information provided through programmatic interfaces is passed-through the data cache module 314 and/or the data cache module 334. Consequently, requests for such data can be fulfilled based on operation of the data cache module 314 and/or the local data cache module 334 in the pass-through mode, as discussed above. In this manner, such patient data/information is not persisted by the data cache module 314, 334.

Although the example of FIG. 3 depicts facility systems 302, 304 having different types of patient record modules 303, 305, it is appreciated that facility systems can include any appropriate combination of types of patient record modules and any number of patient record modules (e.g., patient record modules 303, 305), and respective adapter modules (e.g., modules 326, 336). Further, although the example of FIG. 3 depicts two facility systems, implementations of the present disclosure are applicable in instances include any number of facility systems.

FIG. 4 is a more detailed view of the functional block diagram of FIG. 3, depicting additional components of the example system 300. In the depicted example, the DMS 301 further includes a patient list import module 400, a patient membership portal module 402, a patient matching service module 404, a provider management (mgmt) module 406, a patient information data store 408, and a directory information data store 410. In some examples, the patient information data store 408 stores patient demographic information 420, a data pointer cache 422, a patient-to-provider index 424 and a patient-to-facility index 426. In some examples, the directory information data store 410 stores a facility directory 430, a provider directory 432, and provider-to-facility index 434.

In some implementations, the patient list import module 400 enables initial and ongoing import of patient lists and patient demographic information for patients. In some examples, the patient list import module 400 provides an interface to receive a patient list, e.g., provided in a computer-readable document, and processes the patient list to populate the patient information data store 408 (e.g., the demographic information 420). In some examples, the patient membership portal module 402 provides an interface that enables users (e.g., an administrator) to establish relationships between patient data/information stored across healthcare continua and particular patients. In some examples, healthcare providers, facilities and/or facility systems across healthcare continua can be included in a healthcare organization (e.g., an accountable care organization (ACO)). In some examples, the patient membership portal module 402 enables a user to define relationships between multiple patient records (e.g., based on respective medical record numbers (MRNs)) to the healthcare organization. In some examples, relationship information defined through the patient membership portal module 402 can be stored in the patient information data store 408.

In some implementations, the patient matching service module 404 can be accessed by the host module 312 and the patient membership portal module 402. In some examples, the patient matching service module 404 can be accessed by an application executed on a mobile device (e.g., the mobile device 102) through the host module 312. In some examples, the patient matching service module 404 processes patient data and/or patient information to identify potential patient matches between disparate data sources (e.g., multiple, different EMRs across the healthcare continuum). In some examples, patient information associated with confirmed matches (e.g., confirmed by an administrator through the patient membership portal module 402, confirmed by a healthcare provider using a mobile device through the host module 312) can be stored in the patient information data store 408. In some examples, a patient matching user interface (UI) is provided (e.g., displayed on a mobile device) and can be used by a healthcare provider to search for patients and establish, record and/or confirm relationships between patient records in different systems that are related to a single patient.

In some examples, the demographics information 420 includes information that can be used to identify any patient that has been established in the system. In some examples, the demographics information 420 can be used to search for patients, discussed in further detail herein. Example demographics information can include name, age and/or gender. In some examples, the data pointer cache 422 stores identifiers associated with detailed patient data. In some examples, the identifiers point to particular data stores, in which to be retrieved patient data/information is stored. In this manner, retrieval performance (e.g., speed) can be improved. In some examples, the patient-to-provider index 424 maps particular patients to one or more healthcare providers, and/or particular healthcare providers to one or more patients. For example, a patient can be treated by a plurality of healthcare providers (e.g., members of a patient care team, discussed below). As another example, a healthcare provider can treat a plurality of patients. In some examples, the patient-to-facility index 426 maps particular patients to one or more facilities and/or facility systems. In some examples, a patient can be mapped to particular facilities based on respective MRNs of the patient at the respective facilities. For example, a healthcare continuum for a particular patient can include a hospital and a clinic. In this example, the patient-to-facility index can map the patient to the MRN of the hospital and the MRN of the clinic.

In some implementations, the provider management portal module 406 provides an interface (e.g., web portal) to enable members of a healthcare organization (e.g., ACO) to update healthcare provider directory information and/or healthcare provider-to-facility relationships. For example, a physician can be associated with one or more facility systems of the healthcare organization and credentials (e.g., for log on and/or authentication) can be provided to enable the physician to access patient data/information provided from the one or more facility systems.

In some examples, the facility directory 430 provides a directory of the facilities interfaced to by the system (e.g., the DMS 301). In some examples, the facility directory 430 also provides configuration parameters to enable communication (messaging) between the system and computing devices associated with the respective facilities. In some examples, the provider directory 432 includes a directory of healthcare providers (e.g., nurses, physicians, specialists, and the like) that are able to access patient data/information through the system (e.g., the DMS 301). In some examples, the provider-to-facility index 434 maps each healthcare provider (e.g., in the provider directory) to one or more facilities. For example, a healthcare provider can treat patients at multiple facilities. In some examples, the provider-to-facility index 434 securely stores credentials of healthcare providers for facilities that the healthcare provider is mapped to. For example, a healthcare provider can have first credentials for accessing patient data/information at a first facility, and can have second credentials for accessing patient data/information at a second facility. In some examples, the provider-to-facility index 434 supports single sign-on functionality discussed in further detail herein.

An example data flow will be discussed to illustrate implementations of the present disclosure. It is appreciated that implementations of the present disclosure are equally applicable to other data flows. The example data flow can be initiated in response to a request received from a mobile device (e.g., the mobile device 102). In some examples, the request includes a user identifier, a device identifier, a patient identifier, patient data identifiers, patient information identifiers and additional data identifiers. In some examples, the user identifier can be used to determine the particular user that has issued the request, and the device identifier can be used to determine the particular device that transmitted the request. In some examples, the patient identifier identifies the particular patient that is the subject of the request, the patient data identifiers identify the particular patient data that has been requested, the patient information identifiers identify the particular patient information that has been requested, and the additional data identifiers identify additional data that has been requested. For example, the patient data identifiers can indicate that patient vital data has been requested, and the additional data identifiers can indicate that vitals alarm data and vital data trend visualizations have also been requested.

In the example data flow, the web module 310 receives the request and processes the request to validate the request and to authenticate the user, who submitted the request (e.g., based on the user identifier and/or the device identifier). Upon validation and authentication, the web module 310 provides the request to the host module 312. The host module 312 processes the request, as discussed above. In some examples, it can be determined that patient data/information required to fulfill the request can be provided from the data cache module 314 (e.g., reposed mode). In such examples, the patient data/information is provided to the host module 312 from the data cache module 314. In some examples, it can be determined that that patient data/information required to fulfill the request is to be retrieved from one or more data sources across a healthcare continuum of the patient (e.g., federated mode).

In some examples, if patient data/information required to fulfill the request is to be retrieved from one or more data sources across the healthcare continuum (e.g. federated mode), request information (e.g., assembled by the host module 312, as discussed above) is provided to the adapter module 316 by data cache module 314. In some examples, the adapter module 316 accesses information stored in the directory store 410 to request data from one or more facility systems (e.g., the facility system 304). For example, the adapter module 316 can be aware of which facility systems to retrieve patient data/information from (e.g., based on the patient-to-facility index 426) and can access the provider-to-facility index 434 to retrieve user credentials for the particular provider (e.g., user that issued the request). In this manner, the adapter module 316 can provide appropriate user credentials to respective facility systems for patient data/information retrieval.

In some examples, the adapter module 316 sends requests to identified facility systems, each local request identifying patient data/information and providing appropriate user credentials. In some examples, respective host modules (e.g., the host module 332) of the facility systems receive the requests from the adapter module 316, and can process the requests as similarly discussed above with reference to the host module 312. The respective host modules fulfill the requests and provide the requested patient data/information back to the adapter module 316. In some examples, the adapter module 316 provides the retrieved patient data/information to the host module 312, which completes processing of the request, as discussed above, and provides a response to the mobile device that issued the request.

As discussed at the outset, the present disclosure provides a healthcare provider, or user of the mobile device 102, with secure, remote access to patient data and/or patient information. Example patient data can include physiological data. In some examples, physiological data can be obtained from patient monitoring device(s). In some examples, physiological data can be obtained by a local healthcare provider (e.g., a nurse, or physician measuring blood pressure, temperature, heart rate). In some examples, physiological data can be recorded in one or more patient records (e.g., EMRs). In the example case of a maternity patient, patient data can include delivery progress information such as cervical exam status, membrane status, gravida, para, epidural status, and/or whether the patient is attempting a vaginal birth after cesarean (VBAC). In some examples, the term patient information refers to information corresponding to a particular patient that is, for example, input into the information system 142 by the local healthcare provider. Example patient information can include the patient's name, the name of the doctor(s) assigned to the patient, the nurse(s) assigned to the patient, a facility identification, a patient bed identification, a summary of patient data, and/or chart annotations. The term patient information can also refer to patient information provided from one or more patient records (e.g., EMRs).

The patient data and/or patient information provided to the remotely located user can be provided as real-time data, and/or as historical data and information. The patient data and/or patient information is communicated between the mobile device 102 and the DMS 160, 160' using a secure connection that is established over the network 106. A secure log-in, or sign-on process is provided, which is preferably compliant with the provisions of the Health Insurance Portability and Accountability Act (HIPAA). The secure sign-on authenticates the identity of the user of the mobile device 102 based on a unique user ID and password combination. Both the user ID and the password must be correct in order to establish the secure communication between the mobile device 102 and the DMS 160, 160'.

In some examples, a census, or patient list is provided, which captures a variety of the information and/or data described herein that is associated with each of one or more monitored patients 150. Strip charting is also provided, in which patient data and/or information can be presented to the user in graphical form. In the example case of a maternity patient, a fetal strip and maternal contraction information can be provided for a particular patient 150.

More specifically, the particular patient 150 is selected from the patient list, and the patient information and/or data is subsequently presented. The presented information and/or data can include a fetal strip and maternal contraction waveform, the patient name, the hospital name, the patient room and/or bed number, and the date and time. The strip charting can provide a real-time view of the patient data, as well as a historical view of the patient data. More specifically, the waveform display can be updated in real-time, such that the user of the mobile device 102 observes the patient data as it occurs and/or is recorded. The user can scroll through the waveform display, to view historical patient data, as described in further detail below.

Several navigation features can be provided that enable the user to manipulate a view of the waveform display. In some implementations, the user can zoom in/out of the displayed image. In this manner, the user can view very specific waveform information, and/or other waveform micro-characteristics by zooming in, for example, and/or can view patterns or other waveform macro-characteristics by zooming out, for example. In some implementations, the user can scroll forward or backward through the waveform display. In this manner, the user can view historical patient data.

A patient data display can also be provided. In some implementations, the patient data display can overlay the strip charting described herein. In other implementation, the patient data display can be provided as an overlay, and/or as a separate display. The patient data display can include, but is not limited to, the patient's name, age, fetal gestation, gravida, parity, cervical exam information, and physician name.

Implementations of the present disclosure can be realized on any one of a number of operating systems, or platforms 302 associated with the particular mobile device 102. Example platforms include, but are not limited to, RIM Blackberry, Apple iOS and/or OS X, MS Pocket PC, Win Mobile (Pocket PC, Smartphone), Win Mobile (standard, professional) and/or any other appropriate platforms (e.g., Google Android, and Hewlett-Packard WebOS, Microsoft Windows, Unix, Linux).

As discussed in detail herein, implementations of the present disclosure are directed to systems and methods of providing integrated and unified views of patient data and patient information from disparate data sources and/or products. More particularly, implementations of the present disclosure provide integrated and unified views of patient data and patient information retrieved from across a healthcare continuum. In some examples, the healthcare continuum can include a plurality of disparate clinical data sources. In some examples, a clinical data source can correspond to one or more categories of healthcare services. Example categories can include emergency medical services (EMS), outpatient services, inpatient services, ambulatory services, post-acute services, home services and stand-alone services. Example EMS can include emergency departments (e.g., emergency room (ER) of a hospital), urgent care facilities and transport (e.g., ambulance). Example outpatient services and/or inpatient services can include hospitals and/or critical access hospitals (CAHs). Example ambulatory services can include clinics, physicians groups/offices, surgery centers and pre-acute care. Example post-acute services can include skilled nursing facilities, long-term care hospitals, rehabilitation centers and home healthcare. Example stand-alone services can include imaging centers (e.g., MIR), oncology centers, laboratories, virtual call centers and retail clinics.

Figure 5:
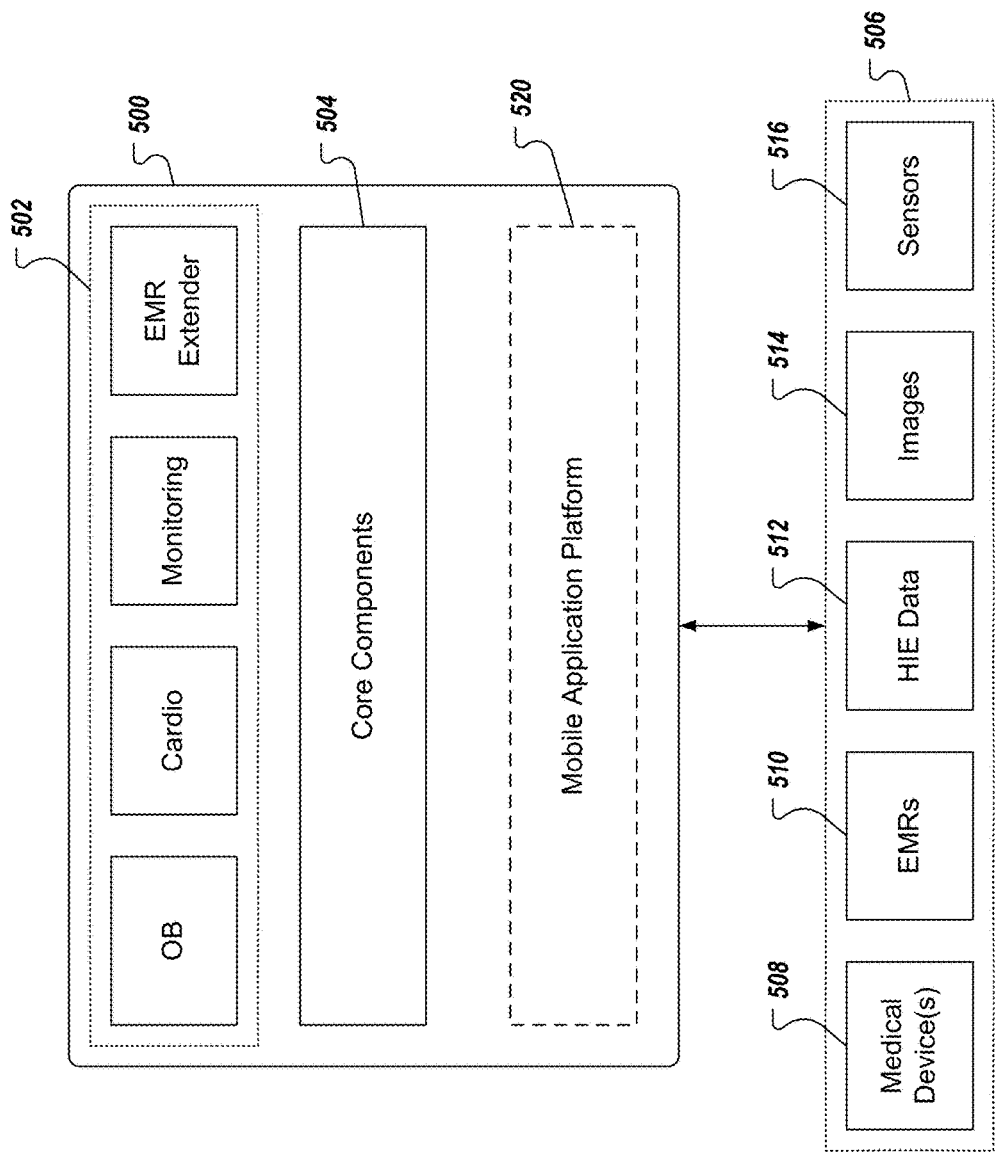
FIG. 5 depicts an example platform for providing integrated and unified views of patient data and patient information.

FIG. 5 depicts an example platform 500 for providing integrated and unified views of patient data and patient information. The example platform 500 includes one or more product applications 502 and core components 504. The example platform enables the transfer of patient data/information to/from one or more data sources 506 for display on a mobile device (e.g., the mobile device 102). In some examples, the example platform 500 is provided as one or more computer-executable programs that are executed using one or more computing devices (e.g., the DMS 160, 160'). Example data sources 506 can include one or more medical devices (e.g., bedside monitors), one or more EMRs, health information exchange (HIE) data 512, image data 514 (e.g., x-ray data), and sensor data 516.

In some implementations, the example platform 500 can include a mobile application platform 520. An example mobile application platform 520 can include the mobile application platform disclosed in U.S. application Ser. No. 13/716,974, filed Dec. 17, 2012, and which claims the benefit of U.S. Prov. App. No. 61/579,954, filed Dec. 23, 2011, the disclosures of which are expressly incorporated herein by reference in their entireties.

In some examples, the mobile application platform 520 separates native graphical user interface (GUI) and operating system components from the application logic. In this manner, the mobile application platform 520 translates and interprets application logic into the native languages of each operating system of mobile devices to/from which patient data/information is to be transferred, and embraces the unique properties, features, function, and usability of each operating system. In some implementations, the mobile application platform 520 embodies a template-based approach, where one or more templates are provided, each template corresponding to a view of patient data/information that is to be presented on a mobile device. In some examples, and as discussed in further detail herein, default templates can be provided, which provide default views of patient data/information. In some examples, custom templates can be provided, and can include templates customized by a user of a mobile device.

In some examples, the mobile application platform 520 processes patient data/information based on a template that defines a view to be displayed on the mobile device. In some examples, the mobile application platform 520 generates instructions for rendering graphics based on the patient data/information and the template, and provides instructions to the mobile device, the mobile device executing the instructions to provide the template-based view of the patient data/patient (e.g., rendering the patient data/information in a view displayed on the mobile device).

In some examples, the product applications 502 can include medical software applications that enable mobility in healthcare. For example, products can enable patient information and patient data (e.g., waveforms and other critical data from EMRs, bedside monitors and devices, pharmacy, lab, and other clinical information systems) to be securely and natively accessed by healthcare provides on mobile devices. Example products can include an obstetrics (OB) product (e.g., AirStrip OB provided by AirStrip Technologies, LLC), a cardiologiy product (e.g., AirStrip CARDIO provided by AirStrip Technologies, LLC), a patient monitoring product (e.g., AirStrip PATIENT MONITORING provided by AirStrip Technologies, LLC), and an EMR extension product (e.g., AirStrip EMR EXTENDER provided by AirStrip Technologies, LLC).

Figure 6:
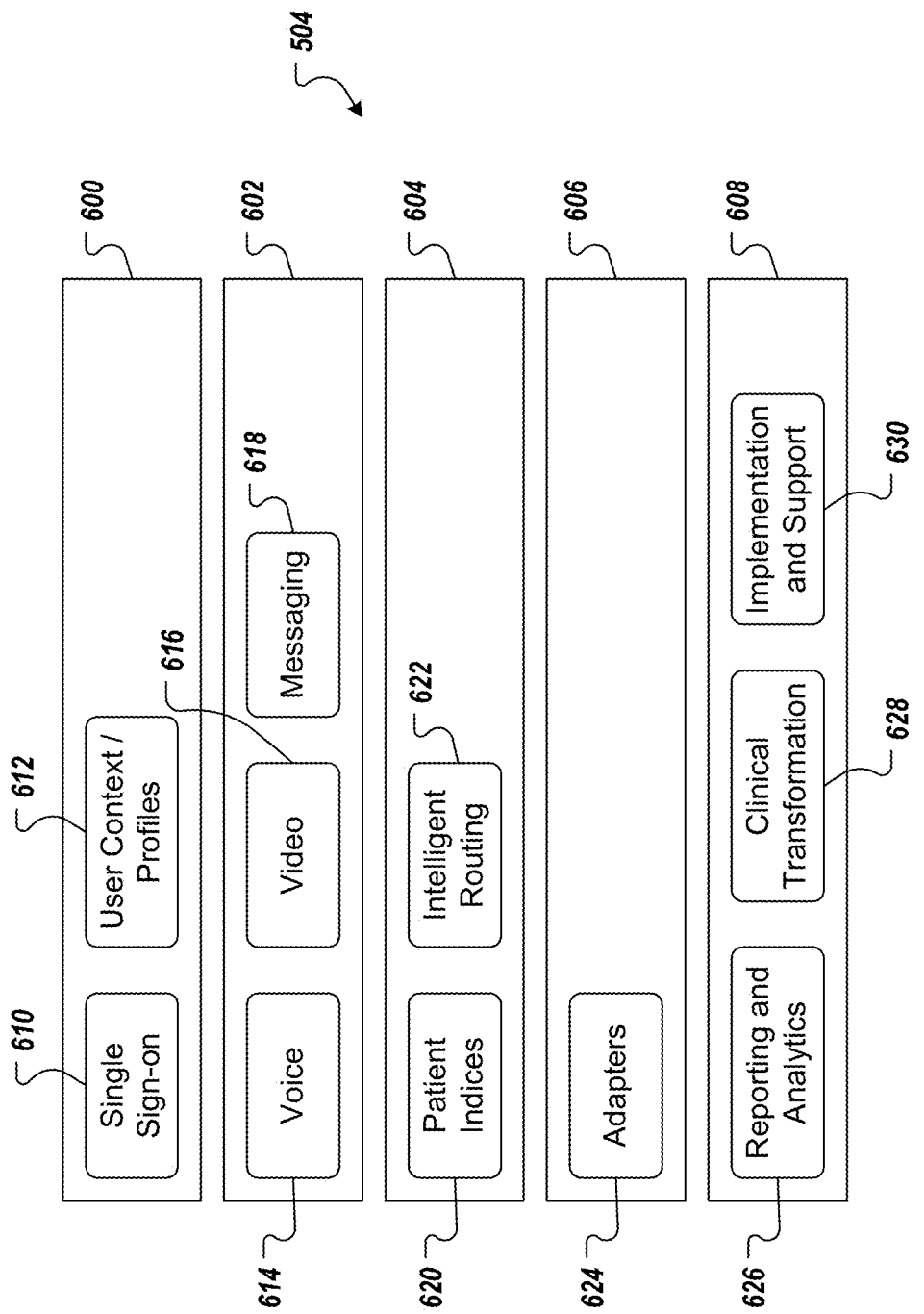
FIG. 6 depicts example components and sub-components that can be included in core components of FIG. 5.

FIG. 6 depicts example components and sub-components that can be included in the core components 504 of FIG. 5.

In some examples, each component and/or sub-component can be provided as one or more computer-executable programs that can be executed using one or more computing devices (e.g., computing devices of the DMS 160, 160' of FIGS. 1 and 2). In some examples, the core components provide secure data access and data transport, single sign-on and profile/context management, interoperability (data adapters and interfaces), intelligent message routing, master patient indices (e.g., EMPI) and care collaboration.

In the depicted example, the core components 504 include a security component 600, a care coordination and collaboration interfaces component 602, a data and workflow integration component 604, a data source adapters component 606 and a services component 608. In the depicted example, the security component 600 includes a single sign-on sub-component 610 and a user context/profiles sub-component 612. In the depicted example, the care coordination and collaboration interfaces component 602 includes a voice sub-component 614, a video sub-component 616 and a messaging sub-component 618. In the depicted example, the data and workflow integration component 604 includes a patient index (or indices) component 620 and an intelligent routing sub-component 622. In some examples, the data source adapters component 606 can include adapter services sub-components 624 (e.g., the adapter services module 324 of FIG. 3). In the depicted example, the services component 608 includes a reporting and analytics sub-component 626, a clinical transformation sub-component 628 and an implementation and support sub-component 630.

In some examples, the single sign-on sub-component 610 supports single sign-on functionality, discussed herein. In some examples, a user can be authenticated once (e.g., by providing log-in credentials to an application executed on a mobile device) and can be provided access to data across a plurality of data sources, without being authenticated for each data source individually. In some examples, the user context/profiles sub-component 612 supports user-specific customizations based on a context of the user and/or a profile of the user, as discussed in further detail herein. Example contexts can include the user being an attending physician at one hospital and a part-time physician at another hospital. In some examples, one or more profiles can be associated with the user, each profile reflecting one or more customizations associated with the particular user. For example, the user can customize a default view that can be displayed on a mobile device, to provide a customized view. Consequently, after the user is authenticated, one or more user-defined (user-customized) views can be provided to the mobile device.

In some examples, the care coordination and collaboration interfaces component 602 supports collaboration between members of a patient care team. For example, a patient care team can include a physician, a consultant, a specialist, an intensivist and a nurse. In some examples, the voice sub-component 614 provides voice-based collaboration between care team members (e.g., teleconferencing). In some examples, the video sub-component 616 provides video-based collaboration between care team members (e.g., video conferencing). In some examples, the messaging sub-component 618 provides messaging-based collaboration between care team members (e.g., SMS/MMS text messaging). In some examples, the care coordination and collaboration component 602 provides security in remote collaboration between care team members (e.g., secure teleconferencing, secure video conferencing and/or secure messaging).

In some examples, the data and workflow integration component 604 integrates data from a plurality of data sources and routes data for display on mobile devices. In some examples, the patient index (or indices) component 620 provides one or more indices for mapping users to facilities and/or patients. In some examples, one or more indices can be provided to associate a user (e.g., a physician) with a facility or multiple facilities (e.g., hospitals), to associate a patient with a facility or multiple facilities, and/or to associate a user with one or more patients. In some examples, an index can be based on an ACO. In some examples, the ACO includes one or more healthcare providers across a healthcare continuum and can provide cross-access to patient data/information. In some examples, the intelligent routing sub-component 622 provides intelligent routing functionality, discussed above.

In some examples, the data source adapters component 606 provides adapter functionality. In the depicted example, the services component 608 includes a reporting and analytics sub-component 626, a clinical transformation sub-component 628 and an implementation and support sub-component 630.

As discussed in further detail herein, patient data and patient information can be provided from one or more disparate patient data sources (e.g., examples depicted in FIG. 5). In some examples, a patient can be associated with one or more healthcare services across the healthcare continuum. Consequently, and for each patient, patient data and patient information can be distributed across the healthcare continuum. For example, a patient can be taken to a hospital by EMS (e.g., ambulance), can be treated in an emergency department of the hospital (e.g., ER), can stay in the hospital on an inpatient basis, can frequent a rehabilitation center (e.g., physical therapy), can be undergoing home healthcare (e.g., home nursing care), and patient samples can be sent to a laboratory for analysis (e.g., blood analysis provided by an external laboratory). In this example, treatment of the particular patient touches multiple facilities across the healthcare continuum, and each facility can generate its own patient data, patient information and patient records (EMRs).

In general, an EMR can be described as a digital medical record provided as an electronic document that can be processed (e.g., read from/written to) by one or more computer programs executed by one or more computing devices. Further, each entity or organization (e.g., clinic, hospital, physician, rehabilitation center, laboratory) that treats a patient can include its own, stand-alone information system that provides an EMR that is specific to the information system. Consequently, multiple, disparate EMRs can be provided for a single patient across the healthcare continuum. Within the context of the example above, a first EMR can be provided for the patient by an ambulance service that transported the patient to the hospital, a second EMR can be provided for the patient by the hospital, a third EMR can be provided for the patient by the rehabilitation center and a fourth EMR can be provided for the patient by a nursing company that is providing home nursing care to the patient. In some examples, and as noted above, EMRs can be generated from disparate information systems. Consequently, format and syntax of one EMR can be different from the format and syntax of another EMR.

In some examples, historical patient data and information can be provided for viewing by a healthcare provider, as well as providing real-time patient data for viewing to the healthcare provider. Extending the example above, the patient can be re-admitted to the hospital on an inpatient basis and can be connected to one or more patient monitoring devices that generate patient physiological data based on patient physiological activity. In accordance with implementations of the present disclosure, and as discussed in further detail herein, patient data and information from one or more of the first EMR, the second EMR, the third EMR and the fourth EMR, as well as real-time patient data can be provided for display to a healthcare provider (e.g., a physician attending to the patient) on a mobile device in an integrated and unified manner. For example, real-time and/or historical patient physiological data can be provided for display by multiple products (e.g., a cardiology product and a patient monitoring product). Implementations of the present disclosure enable integration and unification of the patient physiological data across the products.

In accordance with implementations of the present disclosure, patient data can be displayed to a user of a computing device. In some implementations, the user provides log-in credentials to an application that is executed on the mobile device. For example, the application can open and can provide a log-in screen for the user to provide credentials. In some examples, the credentials can include a personal identification number (PIN). If the PIN is not authenticated (e.g., the user-input PIN is not the same as a pre-stored PIN), an error is displayed. If the PIN is authenticated (e.g., the user-input PIN is the same as a pre-stored PIN), a sites screen or a base screen can be displayed. In some examples, authentication can be provided based on a personal identifier (e.g., the PIN) and another identifier. In some examples, another identifier can include an identifier that is unique to a mobile device that the user is using. For example, the PIN and a unique device identifier can be provided for authentication.

Figure 7:
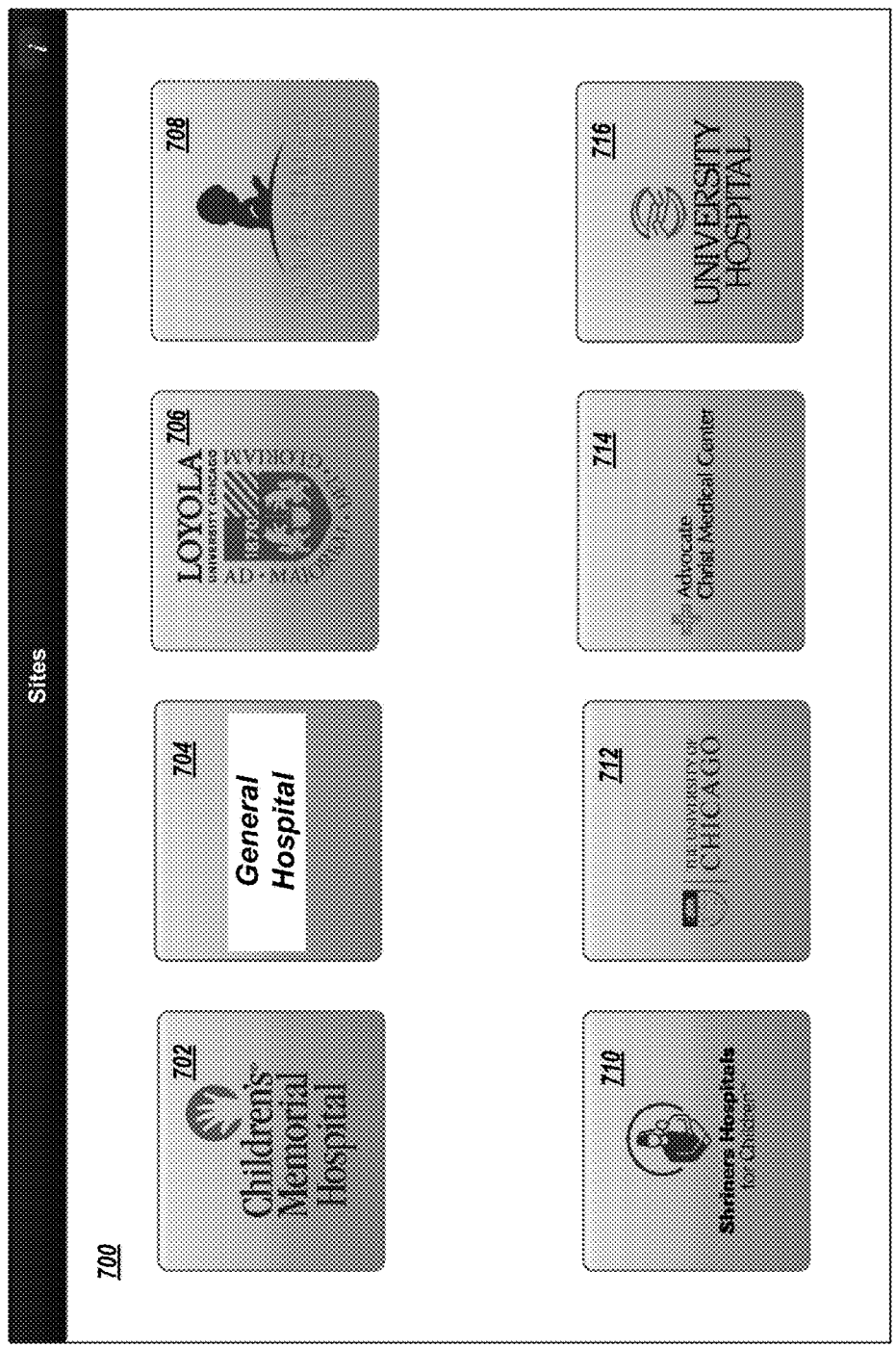
FIGS. 7-16B depict example graphical user interfaces (GUIs) for providing integrated and unified views of patient data and patient information in accordance with implementations of the present disclosure.

FIG. 7 depicts an example sites screen 700. In some implementations, the sites screen 700 provides a GUI including one or more site icons that can be selected (e.g., clicked on) by the user. In some examples, a site can include a specific facility (e.g., hospital clinic), a system of facilities (e.g., a hospital system including one or more hospitals, one or more clinics, and/or one or more laboratories, and the like). In some examples, an index (e.g., a user-facility index) can be accessed based on an identifier associated with the user, to determine the one or more site icons that are to be displayed to the user. In some examples, in response to the PIN being authenticated, an identifier associated with the user can be provided to the DMS 160', for example, by the mobile device 102 (see FIGS. 1 and 2). In some examples, the DMS 160' stores an index (e.g., a user-facility index) that is accessed based on the identifier. In some examples, the index maps the identifier associated with the user to one or more facilities that the user is associated with. In response, the DMS 160' provides instructions to the mobile device 102 to display the sites screen 700 including the one or more site icons 702, 704, 706, 708, 710, 712, 714, 716, each site icon being a graphical representation of a facility of facilities that the user is associated with.

In some implementations, and as noted above, the user can be associated with more than one site (e.g., 702, 704, 706, 708, 710, 712, 714, 716). In some implementations, the user is affiliated with a single site, which is included in a network that includes a plurality of inter-communicating sites associated therewith. In some examples, a site can include a medical center, a dispensary, a hospital, an infirmary, a surgery center, an ambulatory setting, a nursing home, a rest home, a sanatorium, a sanitarium, or any other appropriate healthcare facility. In some implementations, the site screen 700 can provide a summary of each site and/or specific sites, with which the user is associated. In some examples, a site summary can include a plurality of selectable icons (e.g. a site access icon, a site information icon, a patient information icon, etc.). In some implementations, each site summary can include attributes (e.g. patient counts).

User input can be provided to the site screen 700, the user input indicating a selection of a site icon of the one or more site icons. In some examples, user input can include touching of a touchscreen display with a digit (e.g., finger), a stylus, and/or other pointing device, as well as with a digital cursor and/or a keypad.

In some implementations, a base screen can be displayed. In accordance with implementations of the present disclosure, and as discussed in further detail herein, the base screen can include a menu. In some examples, the menu provides a GUI, through which the user can request display of patient data/information. In some examples, the menu is a user-specific menu. In some examples, the menu is specific to one or more user contexts. In some examples, the menu is specific to a site selected by the user. In some examples, the base screen is displayed in response to the PIN being authenticated. In some examples, the base screen is displayed in response to user input to the sites screen.

In accordance with implementations of the present disclosure, the menu is provided as a slide-out menu that is animated in response to user selection of an icon. In some examples, the menu can be animated such that the menu appears to slide-out from an edge of the base screen (e.g., left-side edge). In some examples, the menu is animated such that the menu appears to slide-in to the edge of the base screen in response to user selection of an icon from the menu.

In accordance with implementations of the present disclosure, the menu can include icon groups. In some examples, the icon groups can be provided as default icon groups. For example, a default icon group can be displayed in the menu, the default icon group being agnostic to the particular user (e.g., displayed for any user). In some examples, the icon groups can include user-customized icon groups. For example, the menu can include a user-customized icon group that is specific to (e.g., that was defined by) the user. In some examples, the icon groups can include user-specific and/or site-specific icon groups. For example, an icon group can include a workflow icon group that is specific to the role of the user (e.g., an attending physician) at a specific facility.

Figure 8A:
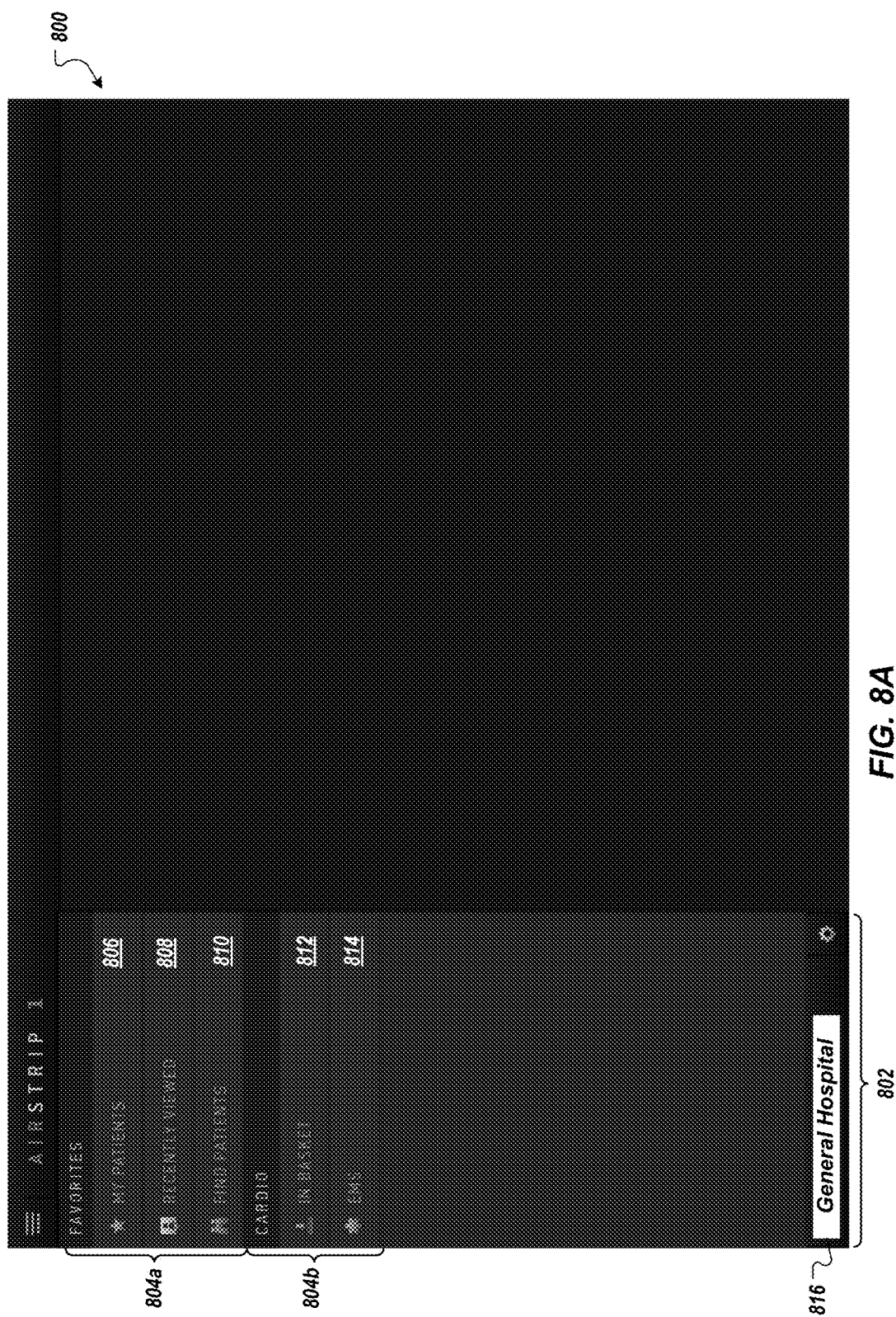
Figure 8B:
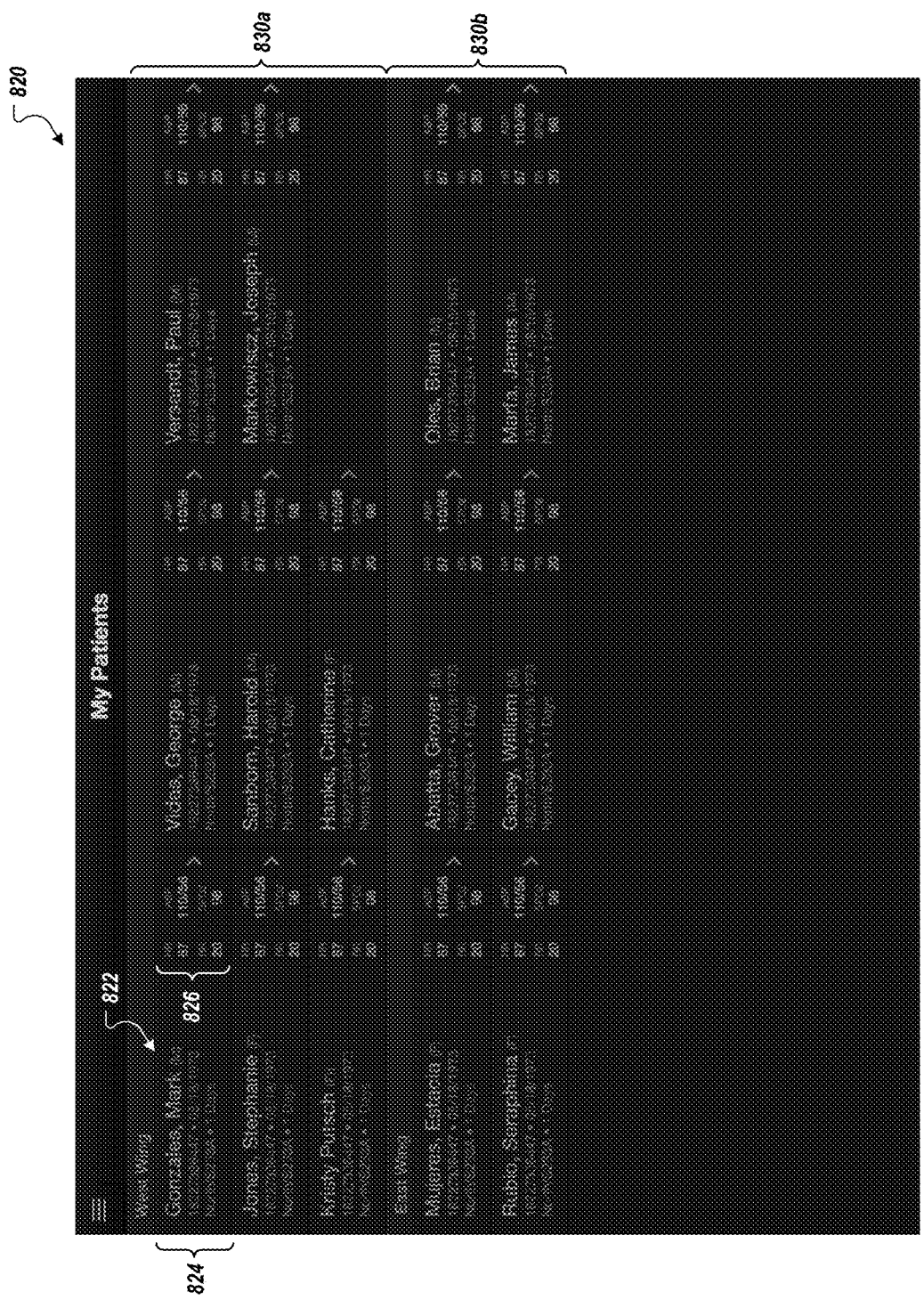

FIGS. 8A and 8B illustrate example screen-shots of a base screen 800 that includes a menu 502. The example base screen 800 of FIGS. 8A and 8B is user-specific and site-specific. For example, the base screen 800 can be displayed in response to user selection of a site icon (e.g., the site icon 704 of FIG. 7). Consequently, a site identifier 816 can be provided to indicate the site, to which the menu 802 is specific. In some examples, a request for the base screen is provided to the DMS 160' in response to user selection of an icon from the sites screen 700. In some examples, the request indicates the site that was selected. In some examples, a user-facility index can be accessed to determine a configuration of a menu to be displayed in the base screen. For example, and for a given site (facility), the user can have an associated profile, user-defined patient groups, context-specific workflows and/or facility-specific workflows. Consequently, the DMS 160' can provide instructions for displaying a user-specific, site-specific base screen, such as the example base screen 800 of FIGS. 8A and 8B. More particularly, the instructions can include instructions for displaying a user-specific, site-specific menu 802 for the base screen 800.

In the depicted example, the menu 802 provides icons for initiating respective displays of patient data/information. In the menu 802, the icons are displayed in icon groups, or menu groups 804a, 804b. It is appreciated that more or fewer icon groups can be displayed. In the example of FIGS. 8A and 8B, the icon group 804a can be provided as a default icon group. For example, the icon group 804a includes icons "My Patients" 806, "Recently Viewed" 808, and "Find Patients" 510. In some examples, the icons 806, 808, 810 are default icons. That is, for example, the icons 806, 808, 810 are not specific to the user and/or the facility (e.g., the icons 806, 808, 810 are displayed regardless of the particular user and/or the particular facility). In some examples, the icon group 804a can be customized by the user. For example, the user can define a patient group (e.g., "My Cardio Patients," "My OB Patients") and can associate one or more patients with the group. Consequently, an icon that is representative of a user-defined group can be displayed in the icon group 804a.

In the example of FIGS. 8A and 8B, the icon group 804b can be provided as a user-specific and facility-specific icon group. For examples, the icon group 804b can be representative of a workflow (e.g., "Cardio") associated with the user at the particular facility (e.g., as indicated by the identifier 816). Consequently, the icon group 804a can include icons that are relevant to the particular workflow. In the depicted example, the icon group 804b includes an "In Basket" icon 812 and an "EMS" icon 814. In some examples, a workflow can include one or more tasks to be performed by the user as part of the user's role at a particular facility.

In some implementations, a request can be provided to the DMS 160' in response to user selection of an icon from the menu 802. In the example of FIGS. 8A and 8B, the user can select the "My Patients" icon 806. In response, a request can be provided to the DMS 160', the request indicating a request for a list of all patients that the user is associated with. The DMS 160' can provide a response that includes instructions to display a list of all patients associated with the user and can include patient data/information for display. In some examples, and in response to the user selection of the "My Patients" icon 806, the menu 802 is animated to slide-in to the edge of the screen.

FIG. 8B illustrates an example screenshot of a "My Patients" screen 820 that can be displayed in response to user selection of the "My Patients" icon 806 of FIG. 8A. In this example, and in response to selecting the "My Patients" icon 806, the screen 820 displays patient icons 822 (graphical representations) for all of the patients that are assigned to the specific user for the particular facility (e.g., General Hospital). In some examples, and in response to the request, the DMS 160' accesses one or more patient indices to identify which patients are assigned to the user at the specified facility. In some examples, the DMS 160' retrieves patient data/information for the identified patient(s) and provides instructions to the mobile device to display the screen 820. In some examples, the DMS 160' retrieves patient data/information from one or more data sources associated with the patient and/or the particular facility. In some examples, patient data/information that is to be displayed in the screen 820 can be retrieved from data storage local to the DMS 160'.

In some examples, an order in which the patient icons are displayed can be determined by a fixed count (e.g., the most recent patients that the user has reviewed), and/or can be determined based on alerts (e.g., the patients that require immediate attention). In some implementations, the user can laterally scroll (as illustrated in FIG. 8B) or vertically scroll to see other patient icons that are not currently viewable on the screen 820.

In the example of FIG. 8B, the patient icons 822 each include patient information 824 and patient data 826. In the depicted example, the example patient information 824 can include patient name, the patient sex, an identifier associated with the patient, and patient date of birth (DOB). In the depicted example, the example patient data can include heart rate (HR), ambulatory blood pressure (ABP), respiratory rate (RR), and oxygen saturation (SPO2). It is appreciated that implementations of the present disclosure can include additional and/or other patient data/information in a patient icon 822. In some examples, the patient data/information provided in the patient icons 822 can include recorded patient data/information. In some examples, the patient data/information provided in the patient icons 822 can include real-time patient data/information. For example, a patient icon 822 can be representative of a patient that is currently being monitored by one or more patient monitoring devices (e.g., as depicted in FIGS. 1 and 2), and the patient data displayed in the patient icon 822 can be updated in real-time based on data provided from the monitoring device(s).

In the example of FIG. 8B, patient icon groups 830a, 830b are provided. In some examples, patient icon groups can correspond to respective locations of the patients within a facility, to which the screen 820 is specific. In the example of FIG. 8B, the screen 820 can be specific to the facility "General Hospital" (e.g., site icon 706 of FIG. 7), and the patient icon groups 830a, 830b correspond to respective wings of the facility (e.g., West wing, East wing, respectively).

In some examples, by selecting the "Recently Viewed" icon 808 of FIG. 8B, a display screen (not shown) can be provided, in which patient icons are provided for patients, whose patient data/information has been recently viewed by the user. In some examples, the patient icons to be included in a "Recently Viewed" patient list can be determined based on a fixed count (e.g., the last X patients that the user has viewed), and/or can be determined based on time (e.g., patients viewed by the user over the last Y hours or day(s)).

As discussed above, the screens 800, 820 of FIGS. 8A and 8B are user-specific and site specific. In some implementations, such screens can be user-specific, but not site-specific. For example, a site-agnostic "My Patients" screen can be displayed and can include patient icons representative of all patients assigned to the user across all facilities that the user is associated with. In some examples, in response to user selection of a "My Patients" icon from not site-specific menu, a request can be provided to the DMS 160'. In some examples, and in response to the request, the DMS 160' accesses one or more patient indices to identify which patients are assigned to the user regardless of facility. In some examples, the DMS 160' retrieves patient data/information for the identified patient(s) and provides instructions to the mobile device to display the site-agnostic "My Patients" screen 820.

Figure 9A:
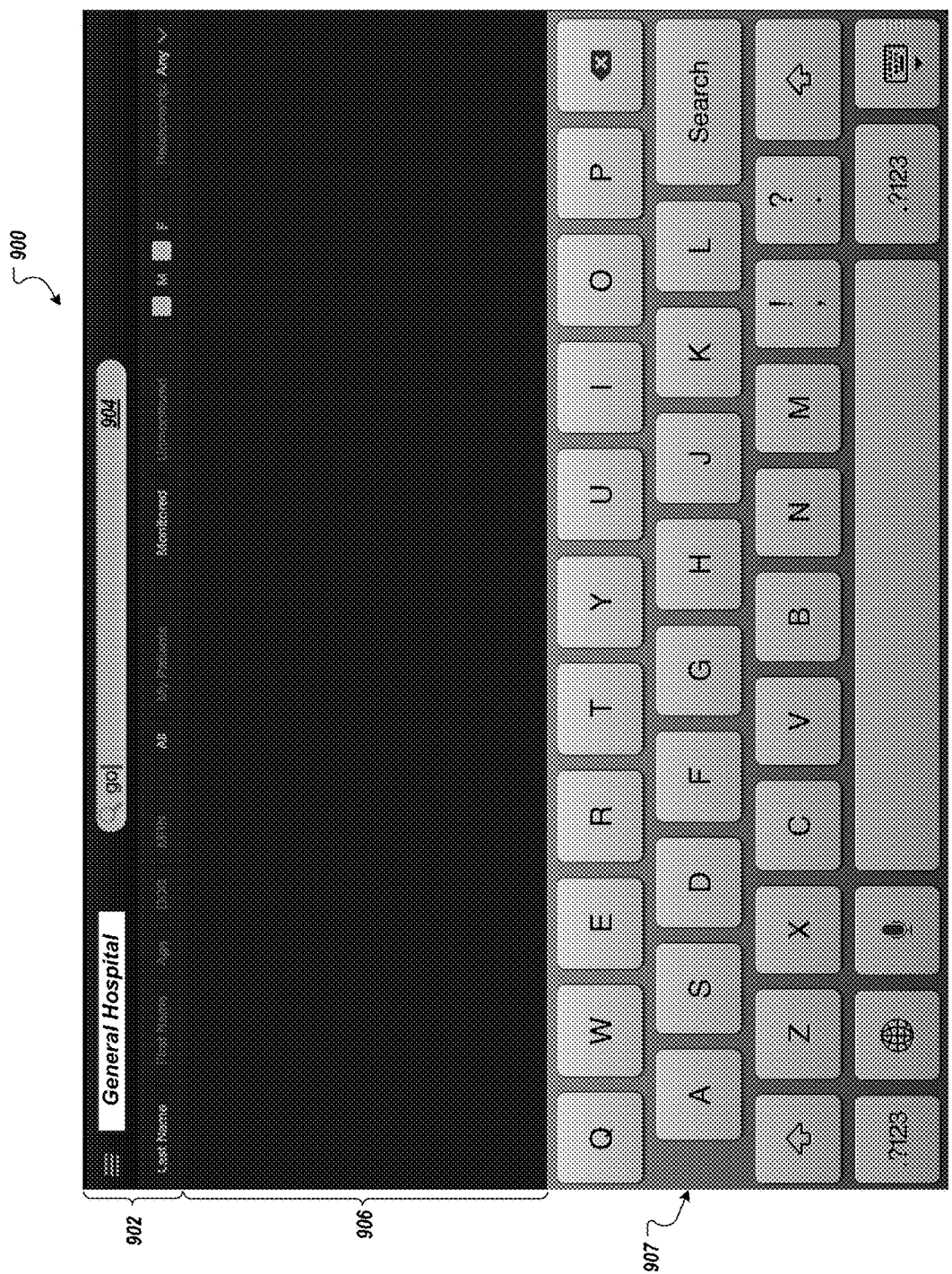
Figure 9B:

In some examples, by selecting a "Find Patients" icon (e.g., the icon 810 of FIG. 8A), a search interface is provided. FIGS. 9A and 9B illustrate example screenshots of a search interface 900. FIG. 9A illustrates the example search interface 900, enabling a user to initiate a search for a particular patient. In the depicted example, the search interface 900 can include a search section 902 that includes a search box 904. In some examples, buttons can be provided to refine the search. For example, the search can be refined based on patient's last name (as illustrated in FIG. 9A), gender, age or other patient specific data. In the depicted example, the search interface 900 includes a search results section 906 to display search results (as discussed in further detail below with reference to FIG. 9B). In some examples, a keyboard 907 is displayed, enabling the user to input a search query (e.g., a patient name or portion thereof). For example, the user can type the first letters of a patient's last name (as illustrated in FIG. 9A).

FIG. 9B illustrates the example search interface 900, providing search results 908 based on user input (e.g., the search query [go]). The search results 908 are displayed in the search results section 906 and include one or more icons (e.g., patient icons 822) associated with patients that are determined to be responsive to the search query.

The example search interface of FIGS. 9A and 9B are user-specific and site specific. In some implementations, such a search interface can be user-specific, but not site-specific. For example, a site-agnostic search interface can be displayed, can receive a search query, and can display patient icons representative of all patients responsive to the search query and assigned to the user across all facilities that the user is associated with.

In accordance with implementations of the present disclosure, the user can select a patient icon (e.g., a patient icon 822). In response to the user selection, a patient screen can be displayed. In some examples, and in response to the user selection of a patient icon, a request is provided to the DMS 160'. In some examples, and in response to the request, the DMS 160' accesses one or more patient indices to identify data sources, from which patient data/information is to be retrieved for the particular patient. In some examples, the DMS 160' retrieves patient data/information for the identified patient from a plurality of data sources and provides instructions to the mobile device to display the patient data/information in a patient screen.

In the example provided above, a first EMR can be provided for a patient by an ambulance service that transported the patient to a hospital, a second EMR can be provided for the patient by the hospital, a third EMR can be provided for the patient by a rehabilitation center and a fourth EMR can be provided for the patient by a nursing company that is providing home nursing care to the patient. Further, the patient can be re-admitted to the hospital on an inpatient basis and can be connected to one or more patient monitoring devices that generate patient physiological data based on patient physiological activity. In accordance with implementations of the present disclosure, patient data/information from one or more of the first EMR, the second EMR, the third EMR and the fourth EMR, as well as real-time patient data can be provided for display to a healthcare provider (e.g., a physician attending to the patient) in a patient screen on a mobile device.

Continuing with the above example, the DMS 160' can access a patient index that maps the patient to one or more data sources (e.g., the first EMR, the second EMR, the third EMR, the fourth EMR, and real-time patient data from monitoring device(s)), from which patient data/information is to be retrieved for display in the patient screen. In some examples, only a sub-set of data sources of the one or more data sources is identified for retrieving patient data/information. For example, it can be determined that, for a currently selected patient view, patient data/information from the second and third EMRs is to be displayed in the patient screen. This is illustrated in the example patient screens discussed in further detail below. Further, it can be determined that retrieved patient data is to be processed to provide analytical data. Example analytical data can include trend data displayed in graphs, as discussed by way of example below.

In some examples, patient screens can be template-based to define which patient data/information is to be displayed in a particular patient screen (e.g., in implementations using the mobile application platform 520 of FIG. 5). In some examples, a template underlying a patient screen can define which patient data/information is to be displayed in which portions of the patient screen. In some examples, a template underlying a patient screen can define analytical data that is to be displayed in portions of the patient screen. In some examples, a template can be provided as a default template. In some examples, a template can be provided as a customized template that is specific to the user of the mobile device. In some examples, a customized template can include a default template that was modified by a user.

Figure 10A:
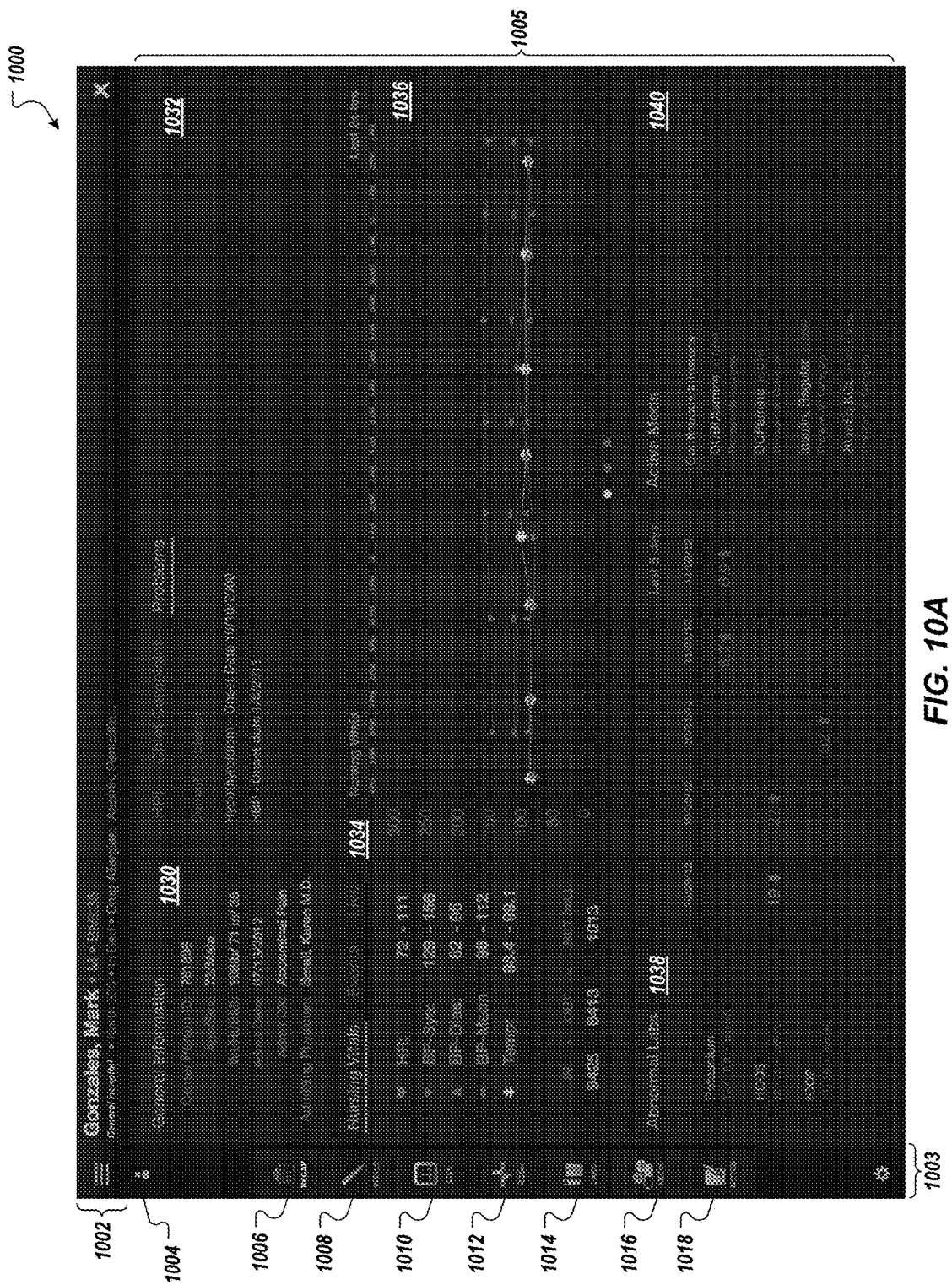
Figure 10B:
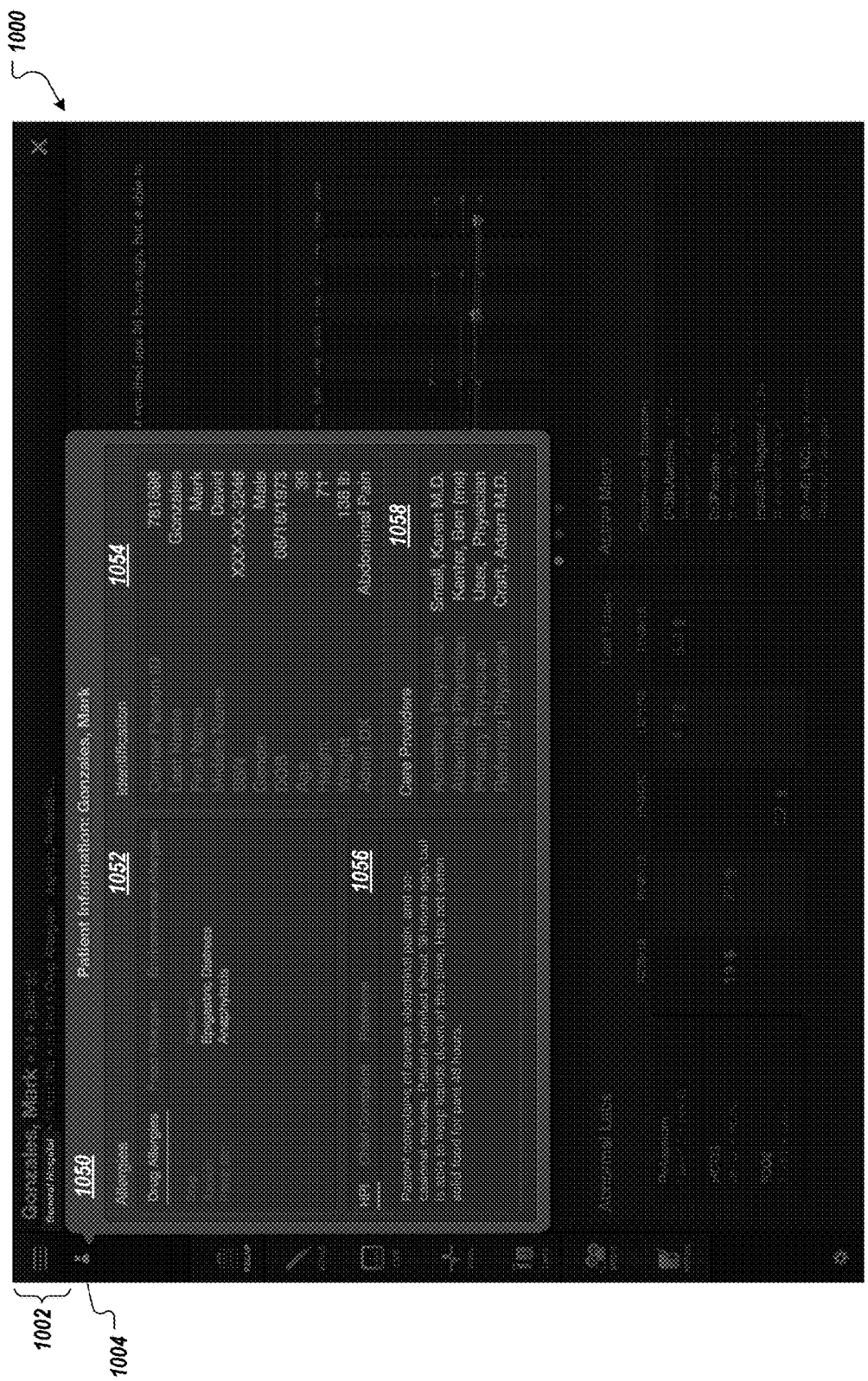
Figure 10C:

Referring now to FIGS. 10A-10C, example patient screens will be discussed. FIG. 10A depicts an example patient screen 1000. In some examples, the patient screen 1000 includes a header 1002, a menu 1003 and a display region 1005. In some examples, the header 1002 includes summary patient information (e.g., patient name, patient body mass index (BMI), patient sex, facility, status, and the like). In some examples, display icons are provided to indicate patient data/information that is to be displayed in the display region 1005. In the depicted example, the display icons include a patient summary icon 1004, a detailed summary icon 1006 ("Recap"), a patient vitals icon 1008, a real-time monitoring icon 1010 ("Live"), an electrocardiogram (ECG) icon 1012, a labs icon 1014, a medications icon 1016 ("Meds") and a notes icon 1018. In some examples, and as discussed in further detail herein, selection of an icon from the menu 1003 prompts the display of particular patient data/information.

In the example of FIG. 10A, detailed summary icon 1006 is selected, and one or more detailed summaries of patient data/information is provided in the display region 1005. In some examples, the detailed summary icon 1006 is provide as a default icon selection in response to the user selection of a particular patient icon (e.g., a patient icon 822 in FIG. 8B). In some examples, the detailed summary screen 1000 is based on a template that defines display sub-regions to be provided in the display region 1005, and the patient data/information and/or analytical data that is to be provided in each of the display sub-regions.

In the example of FIG. 10A, display sub-regions 1030, 1032, 1034, 1036, 1038, 1040. For example, the display sub-region 1030 displays general patient information (e.g., patient identifier, age, sex, height, weight, BMI, date admitted, diagnosis at admittance, and attending physician at admittance). The display sub-region 1032 displays information associated with the current illness/ailment (e.g., history of present illness (HPI), chief complaint and problems). In some examples, the information provided in the display sub-region 1032 can include textual information that is input to by a healthcare provider (e.g., a nurse, an attending physician) into a clinical information system. The display sub-region 1034 displays information associated with vitals for the particular patient (e.g., nursing vitals, events, live). In the depicted example, nursing vitals can include a HR value (e.g., an HR range), a systolic blood pressure (BP-Sys) value (e.g., range), a diastolic blood pressure (BP-Dias) value (e.g., range), a mean blood pressure (BP-Mean) value (e.g., range), and a temperature (Temp) value (e.g., range). The display region 1036 can display graphical trends for the vitals displayed in the sub-region 1034. In the depicted example, "Nursing Vitals" are displayed in the display sub-region 1034. Consequently, the display sub-region displays graphical trends for these vitals. Further, unique markers (e.g., heart-shaped, triangle, square, circle, different colors) can be associated with the vitals in the display sub-region 1034, and can be reflected in the graphical trends in the display sub-region 1036. In this manner, it is easily discerned which graphical trend corresponds to which vital.

In the depicted example, the display sub-region 1038 displays a summary of laboratory results ("labs") that have been determined to be abnormal ("Abnormal Labs"). In some examples, and as depicted in FIG. 10A, the labs data can be displayed in table form based on date. In some examples, the displayed labs data can be color-coded (e.g., blue indicates a decrease in value, red indicates an increase in value). In the depicted example, the display sub-region 1040 displays active medications ("Active Meds") (e.g., medications that the patient is currently prescribed and/or that are being administered to the patient (infusions)).

As noted above, patient screens can be provided based on a template. In some examples, the template is user-specific. For example, in response to selection of a particular patient by the user, the DMS 160' determines the patient screen template to be used based on the user. In some examples, the user-specific template defines which patient data/information is to be displayed in the resultant patient screen. Based on the definition provided in the template, the DMS 160' can retrieve data from one or more corresponding data sources, and, if so defined, can process data to provide analytical data (e.g., graphical trends). The DMS 160' can provide instructions to the mobile device to display the retrieved patient data/information and/or analytical data as defined by the template.

Referring now to FIG. 10B, the detailed patient summary window 1050 can overlay the patient screen 1000. The detailed patient summary window 1050 can be displayed in response to user selection of the patient summary icon 1004. Example patient data/information that can be displayed in the window 1050 can include allergies 1052 (e.g., drug allergies, food allergies, environmental allergies), patient information 1054 (e.g., patient identifier, name (first, middle, last), BMI, gender, DOB, social security number (SSN), age, height, weight, diagnosis at admittance, facility, status, and the like), information associated with the current illness/ailment (symptoms) (e.g., HPI, chief complaint and problems) 1056, and care team member ("Care Providers") 1058. The patient information can be provided as a static list, including multiple tabs per category. For example, the symptoms 724 can displayed as text, divided under multiple tabs corresponding to history of present illness (HPI), chief complains and problems. In some examples, a request is provided to the DMS 160' in response to user selection of the icon 1004, and the DMS 160' retrieves patient data/information from appropriate data sources and provides instructions to the mobile device to display the detailed patient summary window 1050.

Referring now to FIG. 10C, the user can provide user input to the patient screen 1000 to change what patient data/information is to be displayed. In the depicted example, the user has selected "Live" vitals in the display sub-region 1034. In response to the user input, real-time waveform data can be displayed in the display sub-region 1036'. For example, in response to the user selection of "Live" in the display sub-region 1034, a request can be provided to the DMS 160', which can identify one or more data sources that can provide the requested patient data (e.g., based on a patient index). In this example, the one or more data sources can include one or more patient monitoring devices that generate patient data in response to patient physiological activity. In some examples, the patient data is provided for display as a real-time patient data waveform, as disclosed in U.S. Pat. No. 8,255,238, the disclosure of which is expressly incorporated herein by reference in the entirety.

Figure 11A:
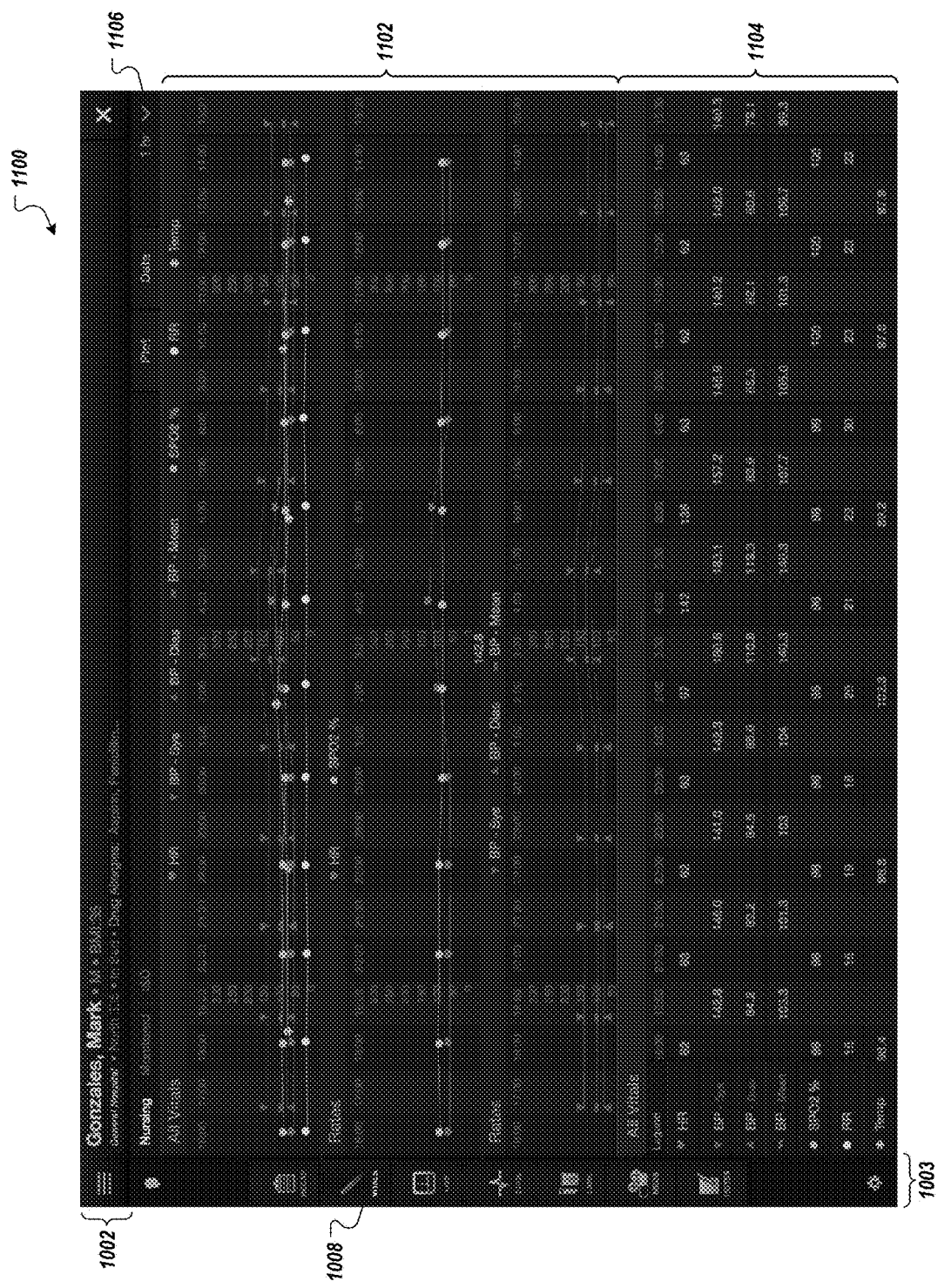

Referring now to FIG. 11A, a vitals screen 1100 is depicted. The vitals screen includes the header 1002 and the menu 1003. In some examples, the vitals screen 1100 is displayed in response to user selection of the vitals icon 1008 (e.g., from the patient screen 1000). In some examples, the vitals screen 1100 can display patient data/information and/or analytical data associated with patient vitals. In the depicted example, the vitals screen 1100 provides a graphical display region 1102 and a tabular display region 1104. In some examples, the data provided in the display regions 1102, 1104 can be includes data retrieved from multiple data sources, as discussed herein.

Figure 11B:
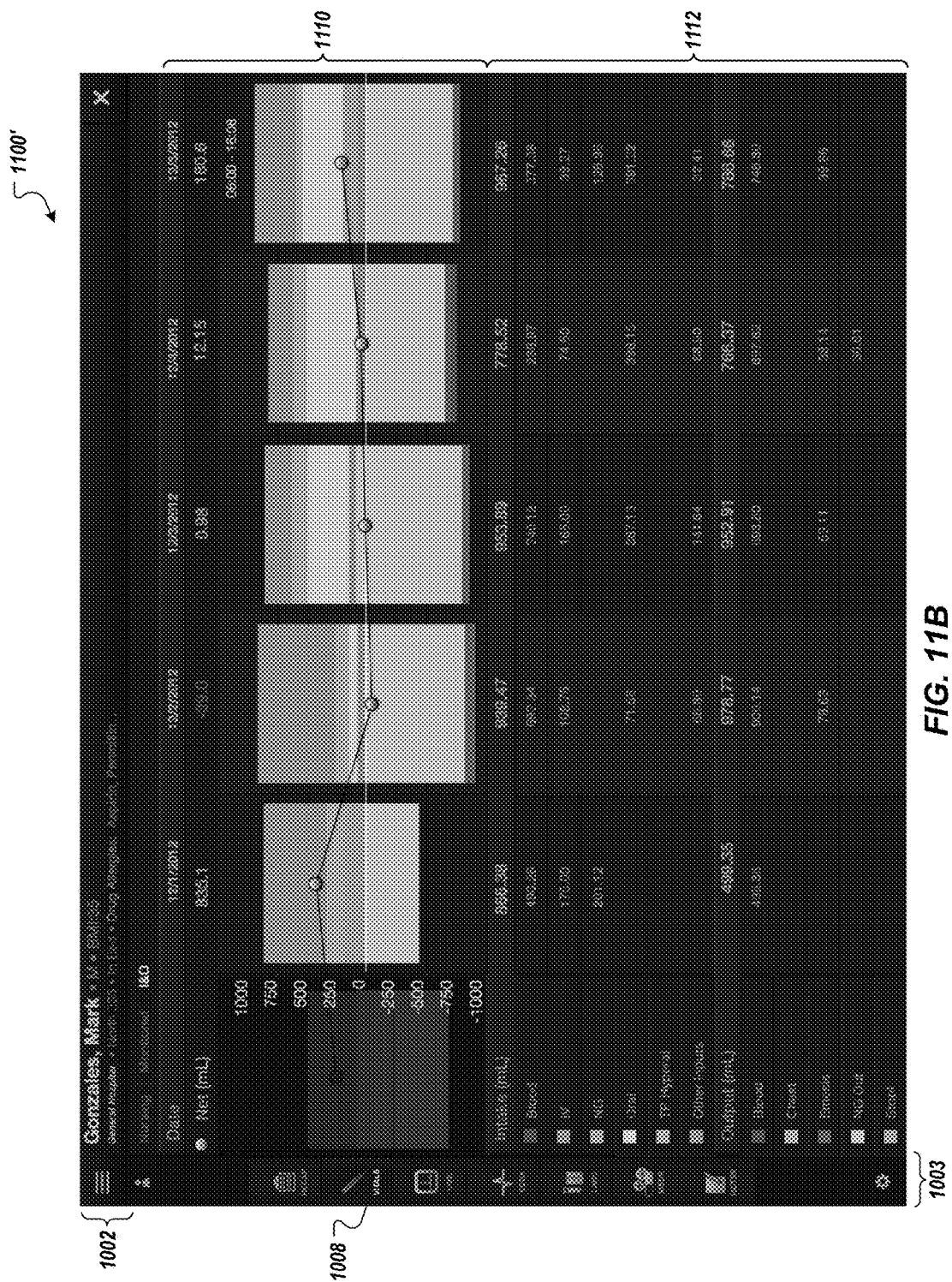

In the depicted example, the display region 1102 displays graphical trends reflecting changes in the data over time, and the display region 1104 displays one or more tables including the data values underlying the graphical trends displayed in the display region 1104. Example vital data includes HR, BP (BP-Sys, BP-Dias, BP-Mean), SPO2%, RR, and body temperature. In some implementations, the vitals display 1100 includes multiple tabs corresponding to a plurality of categories, including nursing vitals (as illustrated in FIG. 11A), monitoring vitals, and input-output (I&O) (as illustrated in FIG. 11B).

In the example of FIG. 11A, a plurality of graphical trends are provided in the display region 1102. In this example, the graphical trends include a graph displaying trend visualizations (e.g., graph series) for all of the monitored vitals, a graph displaying trend visualizations (e.g., graph series) for HR and SPO2% (e.g., a first sub-set of the monitored vitals), and a graph displaying trend visualizations (e.g., graph series) for BP vitals (BP-Sys, BP-Dias, BP-Mean) (e.g., a second sub-set of the monitored vitals). As discussed above, the display region 1104 displays one or more tables including the data values underlying the graphical trends displayed in the display region 1104. In the depicted example, an "All Vitals" table is displayed and corresponds to the "All Vitals" trend graph. It is appreciated that, within the display region 1104, a first "Rates" table can be displayed corresponding to the "Rates" trend graph including HR and SPO2% vitals (e.g., the first sub-set of the monitored vitals), and/or a second "Rates" table can be displayed corresponding to the "Rates" trend graph including BP vitals (BP-Sys, BP-Dias, BP-Mean) (e.g., the second sub-set of the monitored vitals). For example, user input can be provided to the display region 1104 to induce scrolling (e.g., upward, downward) to reveal additional tables.

In some examples, a legend is provided for each graph, the legend depicting which vitals are included in the respective graph and a unique marker associated with each vital. In some examples, the graphs are independently, or collectively scrollable to reveal earlier trending data (e.g., scroll to the right), or later trending data (e.g., scroll to the left). In the example of FIG. 11A, the table displayed in the display region 1104 includes data point values for the vitals displayed in the graphs of the display region 1102. In this manner, the user can see the concrete data values that the trend graphs are based on. Consequently, the trend graphs enable quick recognition of vital trends, and enable the user to identify data points of interest, to review the data underlying the trend graphs from the table.

In some examples, an interval can be changed to provide more detailed or more abstract trend graphs and tables. In the example of FIG. 11A, an example interval includes one hour. Consequently, the trend graphs displayed in the display region 1102 and the table displayed in the display region 1104 are based on one hour increments. In some examples, user input can be provided to the vitals screen 1100 to change the interval. For example, a user can click an icon 1106 and a drop-down menu can be provided, from which the user can select a desired interval (e.g., 1 minute, 15 minute, half hour, 12 hour, 24 hour). In this manner, the user can review finer-grained or higher-level trend graphs and tables.

In some examples, the table is scrollable to reveal earlier data values (e.g., scroll to the right), or later data values (e.g., scroll to the left). In some examples, the trend graph(s) and the table(s) are collectively scrolled. For example, scrolling of a trend graph results in matched scrolling of the corresponding table. As another example, scrolling of a table results in matched scrolling of the corresponding trend graph. In this manner, the data values underlying points on the trend graph remain synchronized with the trend graph. In some implementations, scrolling can be provided in response to user input. In some examples, scrolling in response to a user swiping action on the touchscreen. For example, a user can swipe a touchscreen in a left-to-right direction to induce scrolling backward in time. As another example, a user can swipe the touchscreen in a right-to-left direction to induce scrolling forward in time.

FIG. 11B depicts another example vitals screen, an I&O screen 1100' that can be displayed in response to user selection of the I&O tab (e.g., from the vitals screen 1100 of FIG. 11A). In FIG. 11B, the I&O screen 1100' includes a graph display region 1110 and a table display region 1112. In some examples, the I&O screen 1100' of FIG. 11B depicts patient intake and output of fluids and/or solids in both graphical form (displayed in the display region 1110) and tabular form (displayed in the display region 1112). In some examples, an interval can be changed to provide more detailed or more abstract graphs and tables. In the example of FIG. 11B, an example interval includes one day. Consequently, the bar graphs displayed in the display region 1110 and the table displayed in the display region 1112 are based on one day increments. In some examples, user input can be provided to the I&O screen 1100' to change the interval. For example, a user can select a desired interval (e.g., 1 hour, 12 hours, 1 week, 1 month). In this manner, the user can review finer-grained or higher-level graphs and tables.

As noted above, with respect to patient screens, vital screens can be provided based on a template. In some examples, the template is user-specific. For example, in response to selection of the vitals icon 1008 by the user, the DMS 160' determines the vitals screen template to be used based on the user. In some examples, the user-specific template defines which graphs and/or tables are to be displayed in the resultant vitals screen. Based on the definition provided in the template, the DMS 160' can retrieve data from one or more corresponding data sources, and, if so defined, can process data to provide analytical data (e.g., graphical trends). The DMS 160' can provide instructions to the mobile device to display the retrieved patient data/ information and/or analytical data as defined by the template.

Figure 12A:
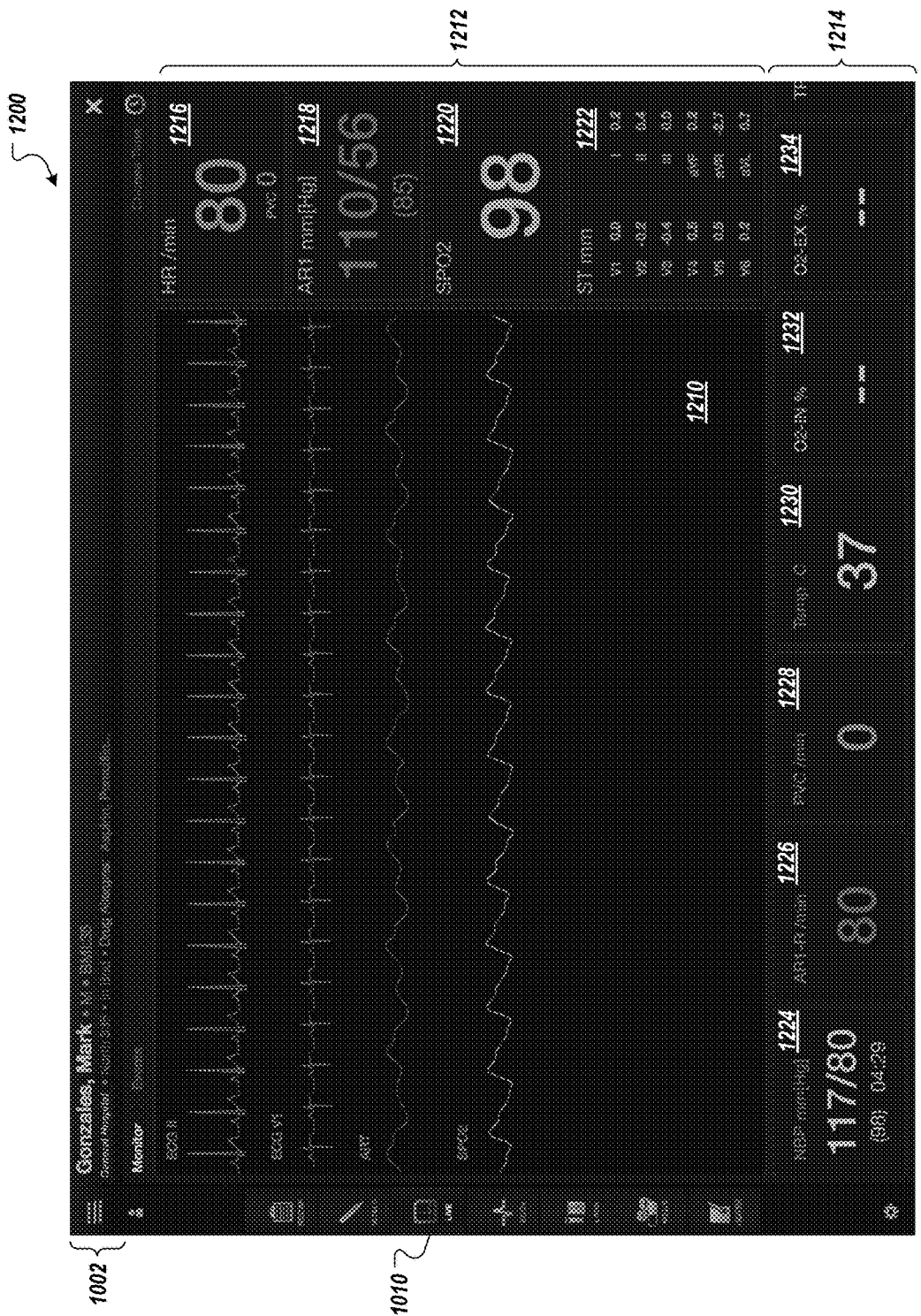
Figure 12B:

FIGS. 12A and 12B depict example monitoring screens 1200, 1202, respectively. With particular reference to FIG. 12A, the monitoring screen 1200 can be displayed in response to user selection of the real-time monitoring icon 1010. In some examples, patient physiological parameters can be monitored by one or more monitoring devices, which are responsive to patient physiological activity and generate patient physiological data based thereon (see FIGS. 1 and 2). As provided in above-referenced U.S. Pat. No. 8,255,238, the patient physiological data can be transmitted to the mobile device to provide real-time monitoring of patient physiological data.

In some examples, the monitoring screen 1200 includes a real-time waveform display region 1210, and real-time textual display regions 1212, 1214. In the depicted example, the display region 1212 includes display sub-regions 1216, 1218, 1220, 1222, each of which is associated with a respective patient physiological parameter being monitored. In the depicted example, the display region 1214 includes display sub-regions 1224, 1226, 1228, 1230, 1232, 1234, each of which is associated with a respective patient physiological parameter being monitored. In some examples, the display sub-regions 1224, 1226, 1228, 1230, 1232, 1234 within the display region 1214 to reveal addition display sub-regions and associated patient physiological parameters being monitored.

In some examples, the monitoring screen 1202 displays discrete events associated with monitored patient physiological parameters. In some examples, the monitoring screen 1202 can be displayed in response to user selection of an events icon 1280 in the monitoring screen 1200 (FIG. 12A). In general, the monitoring screen 1202 displays patient data and/or waveforms associated with one or more events. In some examples, an event can be triggered in response to monitored patient data falling below or exceeding a pre-defined threshold (e.g., an alarm). In some examples, an event can be triggered in response to recognition of a pattern (e.g., one or more sub-events occurring within a pre-determined threshold time of one another).

In the example of FIG. 12B, the monitoring screen 1202 includes display regions 1250, 1252, 1254, 1256, 1258. In some examples, the display regions 1250, 1252, 1254, 1256, 1258 are scrollable (e.g., vertically) to reveal additional display regions. In some examples, each display region 1250, 1252, 1254, 1256, 1258 is associated with a respective time interval. In the depicted example, the display region 1250 is associated with events that have occurred in the past hour, the display region 1252 is associated with events that have occurred 1-2 hours ago, the display region 1254 is associated with events that have occurred 2-3 hours ago, the display region 1256 is associated with events that have occurred 3-4 hours ago, and the display region 1258 is associated with events that have occurred 4-5 hours ago.

In some examples, event summaries are provided and can include waveform data and/or textual data associated with the respective event. In the example of FIG. 12B, event summaries 1260*a*-1260*i* are displayed. In some examples, event summaries can include a priority indication (e.g., high (H), medium (M), low (L)). In some examples, the priority can be provided based on a severity of the event and/or a type of event. For example, if a monitored patient physiological parameter exceeds a threshold by a first amount, a low priority event can be triggered, if the monitored patient physiological parameter exceeds the threshold by a second amount (greater than the first amount), a medium priority event can be triggered, and if the monitored patient physiological parameter exceeds the threshold by a third amount (greater than the second amount), a high priority event can be triggered. In some examples, a patient physiological parameter can have particular importance. Consequently, if the patient physiological parameter exceeds a threshold, regardless of by what amount, a high priority event is triggered. In some examples, a patient physiological parameter can have less importance. Consequently, if the patient physiological parameter exceeds a threshold, regardless of by what amount, a low or medium priority event is triggered.

Each event summary 1260a-1260i provides relevant patient data and waveform data associated with the respective event. In some examples, and within each discrete event summary 1260a-1260i, the user can scroll the waveform data, for example, forward or backward in time to reveal waveform data before or after the event.

In accordance with implementations of the present disclosure, monitoring screens can be provided based on respective templates. In some examples, the template is user-specific. For example, in response to selection of the real-time monitoring icon 1010 by the user, the DMS 160' determines the real-time monitoring screen template is to be used based on the user. In some examples, the user-specific template defines which waveforms and/or textual patient data is to be displayed in the resultant monitoring screen. Based on the definition provided in the template, the DMS 160' can retrieve data from one or more corresponding data sources. The DMS 160' can provide instructions to the mobile device to display the retrieved data as defined by the template. In the case of real-time waveforms, the DMS 160' can continuously provide real-time data from a data source (e.g., a monitoring device) for display as a waveform in the monitoring screen.

Figure 13:
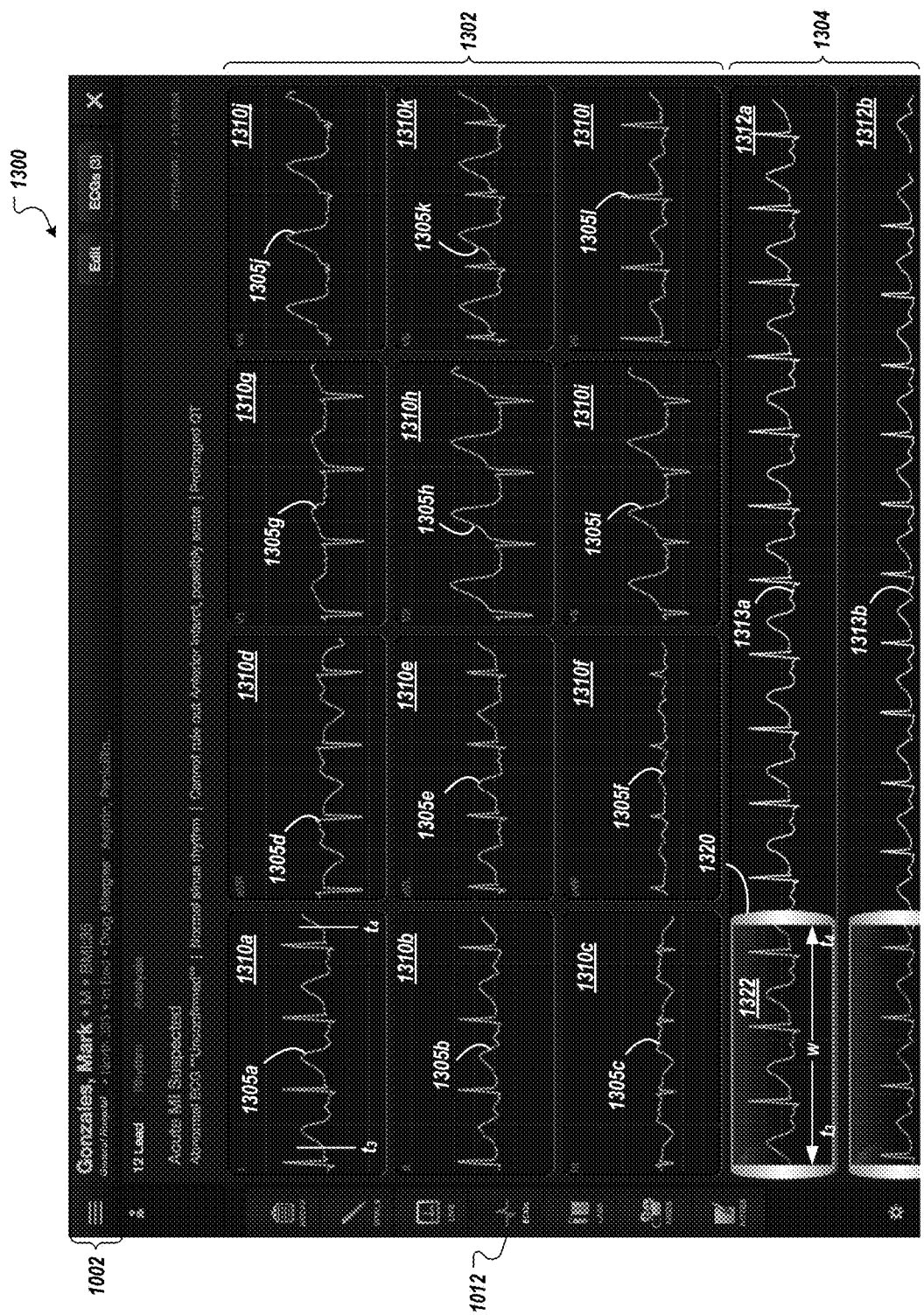

FIG. 13 depicts an example ECG display 1300 graphically representing an ECG on the display of a mobile device. In some examples, the ECG screen is displayed in response to user selection of the ECG icon 1012. The example ECG discussed herein corresponds to a 12-lead ECG. Implementations of the present disclosure are applicable to any appropriate type of ECG. The ECG screen 1300 provides graphical information relating to the data collected from a patient monitoring device. In particular, the ECG screen 1300 provides cardiology information relating to data collected from an ECG monitoring device coupled to a patient.

The ECG screen 1300 includes a display region 1302 and a display region 1304. In the depicted example, the display region 1302 provides a grid of ECG trace windows 1310a-1310l (e.g., 4 columns by 3 rows, the first column including the leads I, II and III, the second column including the leads aVR, aVL and aVF, and the last two columns including the leads $V_1$-$V_6$). Each trace window 1310a-1310l includes a respective voltage trace 1305a-1305l corresponding to the respective lead over a period of time. In some examples, the trace windows 1310a-1310l can be used to zoom in and out of and to scroll along segments of the respective voltage traces 1305a-1305l.

The display region 1304 includes expanded trace windows, each expanded trace window corresponding to a trace window provided in the display region 1302. In the example of FIG. 13, expanded trace windows 1312a, 1312b are displayed and correspond to the trace windows 1310a, 1310b, respectively, of the display region 1302. In some examples, the expanded traced windows can be scrolled upward/downward within the display region 1304 to reveal additional expanded trace windows. For example, un-displayed expanded trace windows (e.g., expanded trace windows 1312c-1112l), or partially displayed, expanded trace windows (e.g., expanded trace window 1312b) can be scrolled into full view, while displayed trace windows (e.g., expanded trace windows 1312a, 1312b) can be scrolled from view.

The display region 1304 can display expanded trace windows 1312a-1312l having respective voltage traces 1313a-1113l, each voltage trace 1313a-1313l corresponding to voltage traces 1305a-1305l. The voltage traces 1313a-1313l are each provided as full traces for a particular period of time, graphically representing the ECG data collected over the particular period of time. In some examples, the user defines a desired time period for viewing ECG data by zooming in/out of and/or scrolling along one of the voltage traces 1305a-1305l to display a desired segment of the voltage traces 1305a-1305l within the trace windows 1310a-1310l. Accordingly, the trace display windows 1310a-1310l respectively display segments of the voltage traces 1305a-1305l, the segments corresponding to respective segments of the voltage traces 1313a-1313l displayed in the expanded trace windows 1312a-1312l. That is, each trace window 1310a-1310l can display a full trace or zoomed-in voltage trace 1305a-1305l corresponding to a voltage trace 1313a-1313l. In some examples, the voltage traces 1305a-1305l are synchronized with each other, such that scrolling and/or zooming of a voltage trace 1305a-1305l in one trace window 1310a-1310l results in an equivalent scrolling and/or zooming in each of the other trace windows 1310a-1310l. Consequently, each trace window 1310a-1310l displays its respective voltage trace 1305a-1305l for the same time period.

With continued reference to FIG. 13, a beveled scrubber bar 1320 can be provided in each of the trace windows 1312a-1312l. The beveled scrubber bar 1320 provides a viewing area 1322 having a width w. The viewing area 1322 displays a portion of the voltage trace 1313a-1313l corresponding to the portion of the voltage trace 1305a-1305l displayed in trace display windows 1310a-1310l. Accordingly, the width w generally corresponds to the time period of the voltage traces 1305a-1305l. In the example of FIG. 13, the width w corresponds to the time period between time $t_3$ and $t_4$. The beveled scrubber bars 1320 provide a graphical indicator that enables a user to quickly discern which portion of the voltage traces 1313a-1313l correspond to the voltage traces 1305a-1305l.

Further details of example ECG displays are provided in International App. No. PCT/US2012/021677, which claims the benefit of U.S. Prov. App. No. 61/433,824, the disclosures of which are expressly incorporated herein by reference in their entireties.

Figure 14A:
Figure 14B:
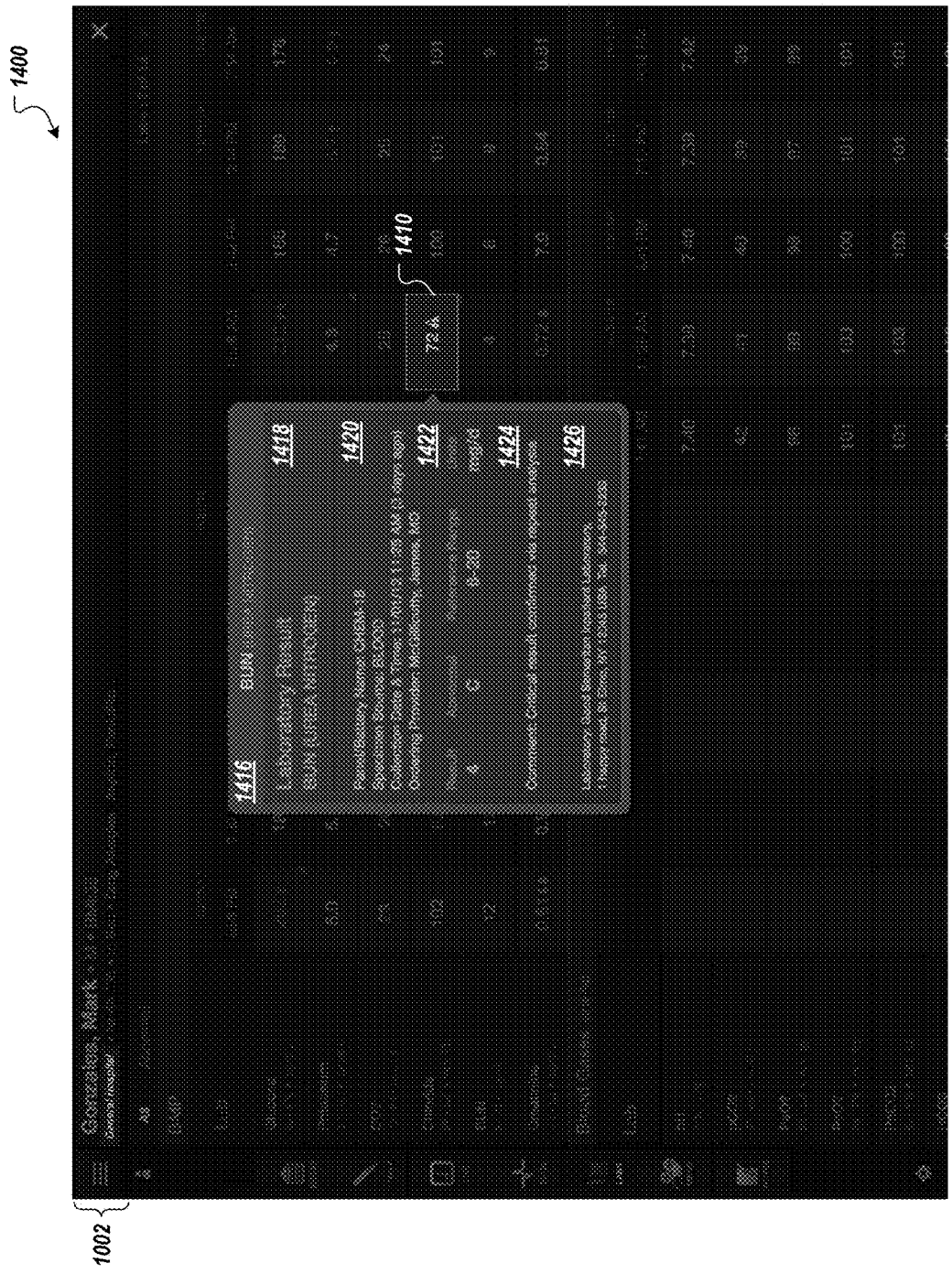
Figure 14C:

FIGS. 14A-14C depict example implementations of a laboratory ("labs") screen 1400 that displays laboratory data associated with a patient. In some examples, the labs screen 1400 is displayed in response to user selection of the labs icon 1014. Example labs that can be displayed include basic metabolic panel (BMP) (e.g., glucose, potassium, $CO_2$, chloride, blood urea nitrogen (BUN), creatinine, and the like), venous blood gases, lipids, arterial blood gases (e.g., pH, $pCO_2$, $PaCO_2$, $pO_2$, $PaO_2$, $HCO_3$, $tCO_3$, and the like), glucose panels, electrolytes, hypothyroid, renal function, and hepatic function among others.

In the depicted examples, the labs screen 1400 includes multiple display regions 1402, 1404, each display region corresponding to a respective labs panel. For example, the display region 1402 displays BMP, and the display region 1404 displays arterial blood gases. In some examples, the display regions are scrollable (e.g., up/down) to reveal additional display regions and corresponding labs panels. In the depicted example, labs data within a labs panel is displayed based on an associated time/date. In some example, the time/date corresponds to a time/date that a sample (e.g., blood sample, urine sample) was taken from the patient.

Further, and within a display region, the lab results can be scrolled (e.g., up down and/or left right) to reveal additional labs results. For example, the display region 1404 of FIG. 14A provides partial lab results for HCO3. Within the display region 1404, the user can scroll the lab results upward to reveal the full data values for the HCO3 lab results, as well as additional lab results (e.g., tCO3 that resides outside of the display region 1404 in FIG. 14A). In some examples, lab results within a display region can be scrolled left/right to reveal result values later/earlier in time/date.

In accordance with implementations of the present disclosure, data values can be color-coded and/or annotated within the display regions. In some examples, a data value that is out of a normal range (e.g., as determined by the laboratory that provides the lab results) can be indicated based on color and/or annotation. In the depicted example, a value that the laboratory has determined is above the normal range includes an upward pointing arrow annotation, and is colored red. In the depicted example, a value that the laboratory has determined is below the normal range includes a downward pointing arrow annotation, and is colored blue. In some examples, a data value severely above or below normal range (e.g., as determined by the laboratory) can be indicated using multiple annotations (e.g., double arrows). In some examples, the laboratory can determine that a data value is deserving of a textual note and, when this occurs, such notable data values can be indicated based on color and/or annotation. In the depicted example, a data value can visually indicated with a warning annotation (e.g., exclamation point within a triangle) and is colored orange. In some examples, the laboratory can determine that a data value should be visually indicated with a warning annotation and can provide a textual note that can be displayed to the user (e.g., in response to user input to the data value).

In accordance with implementations of the present disclosure, labs screens can be provided based on respective templates. In some examples, the template is user-specific. For example, in response to selection of the labs icon 1014 by the user, the DMS 160' determines the labs template is to be used based on the user. In some examples, the user-specific template defines which labs data is to be displayed in the resultant labs screen. Based on the definition provided in the template, the DMS 160' can retrieve labs data from one or more corresponding data sources. The DMS 160' can provide instructions to the mobile device to display the retrieved data as defined by the template. In some examples, the DMS 160' can process the data to identify data, for which indications and/or annotations should be provided. In such examples, instructions provided to the mobile device can include instructions for indicating (e.g., color-coding) and/or annotating (e.g., up arrow(s), down arrow(s), warning symbol) respective data values.

In some implementations, and as depicted in the example of FIG. 14B, the user can interact with displayed data values to retrieve more detailed information. In the example of FIGS. 14A and 14B, the user can provide user input (e.g., touch) to the data value 1410. In response to the user input, a window 1416 can be displayed. In some examples, the window 1416 provides more detailed information on the labs data. In the depicted example, the window 1416 provides the name of the laboratory result 1418, collection information (e.g., panel name, specimen source, device name, ordering provider and collection date and time) 1420, result value 1422, comments 1424 and contact data 1426 (e.g., of the laboratory that generated the labs result). In some implementations, the user can click on the comments section 1424 to edit, add and/or delete comment data.

In accordance with implementations of the present disclosure, a labs data window (e.g., the window 1416) can be provided based on respective templates. In some examples, the template is user-specific. For example, in response to selection of the particular data value 1410 displayed in the labs screen 1400 by the user, a request is sent to the DMS 160', and the DMS 160' determines the window template that is to be used. The DMS 160' can retrieve the more detailed labs data that is to be displayed in the window from one or more corresponding data sources. The DMS 160' can provide instructions to the mobile device to display the window including retrieved data.

In some examples, the user can customize which lab data is displayed in the labs screen 1400. In some examples, and in response to user selection of a menu icon 1412, a drop-down menu 1450 is displayed (see FIG. 14C). In some examples, the drop-down menu provides a list of lab data that can be displayed in the display screen 1400. In some examples, and as depicted in FIG. 14C, the user can check checkboxes associated with labs data that the user would like displayed in the labs screen 1400. In some examples, and in response to the user selection (e.g., the user clicking the "Done" button), a message is sent to the DMS 160' indicating the labs data that is to be displayed in the labs screen. In response to the message, the DMS 160' can provide corresponding labs data and instructions for displaying the labs data in the labs screen 1400.

Figure 15A:
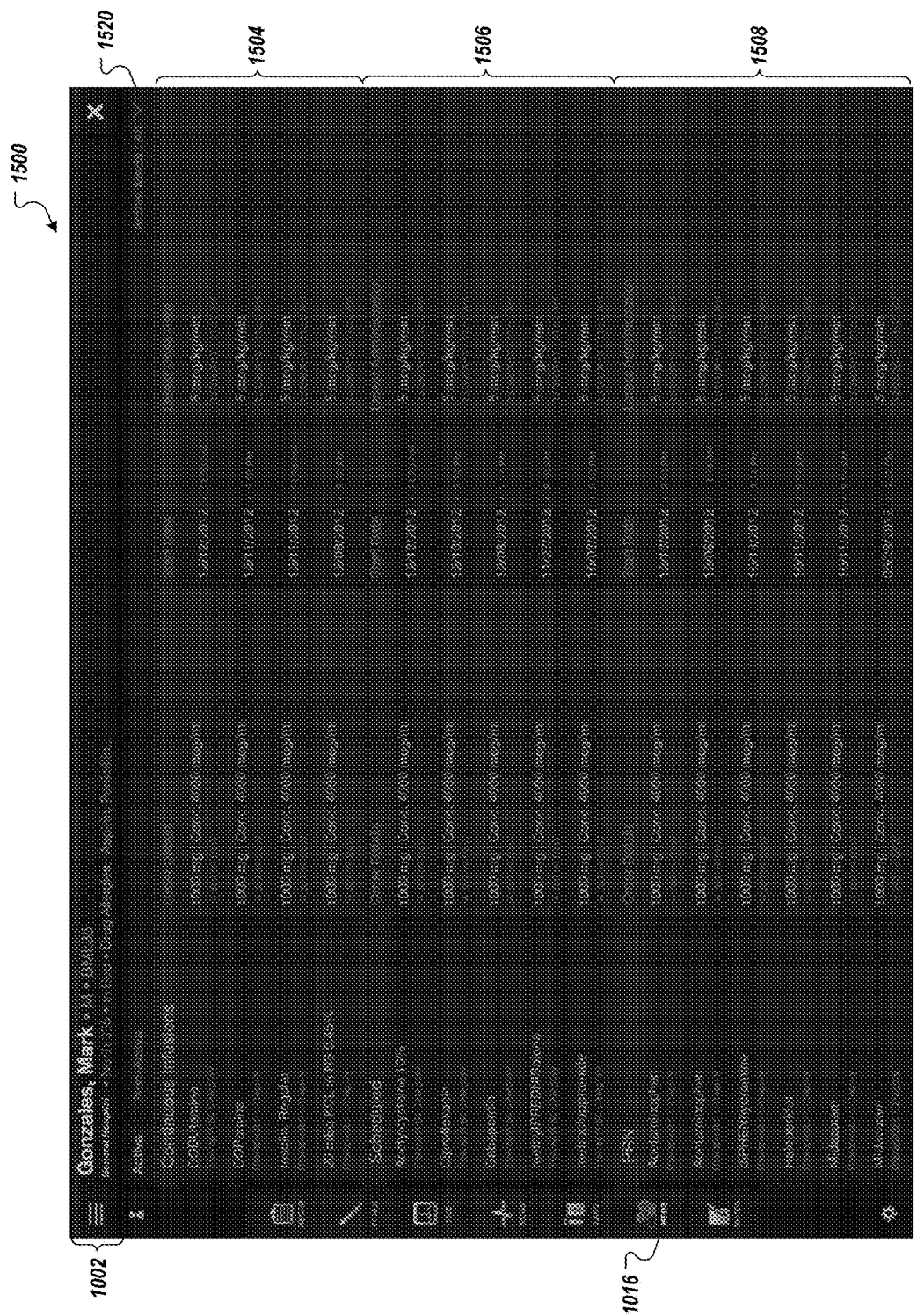
Figure 15B:
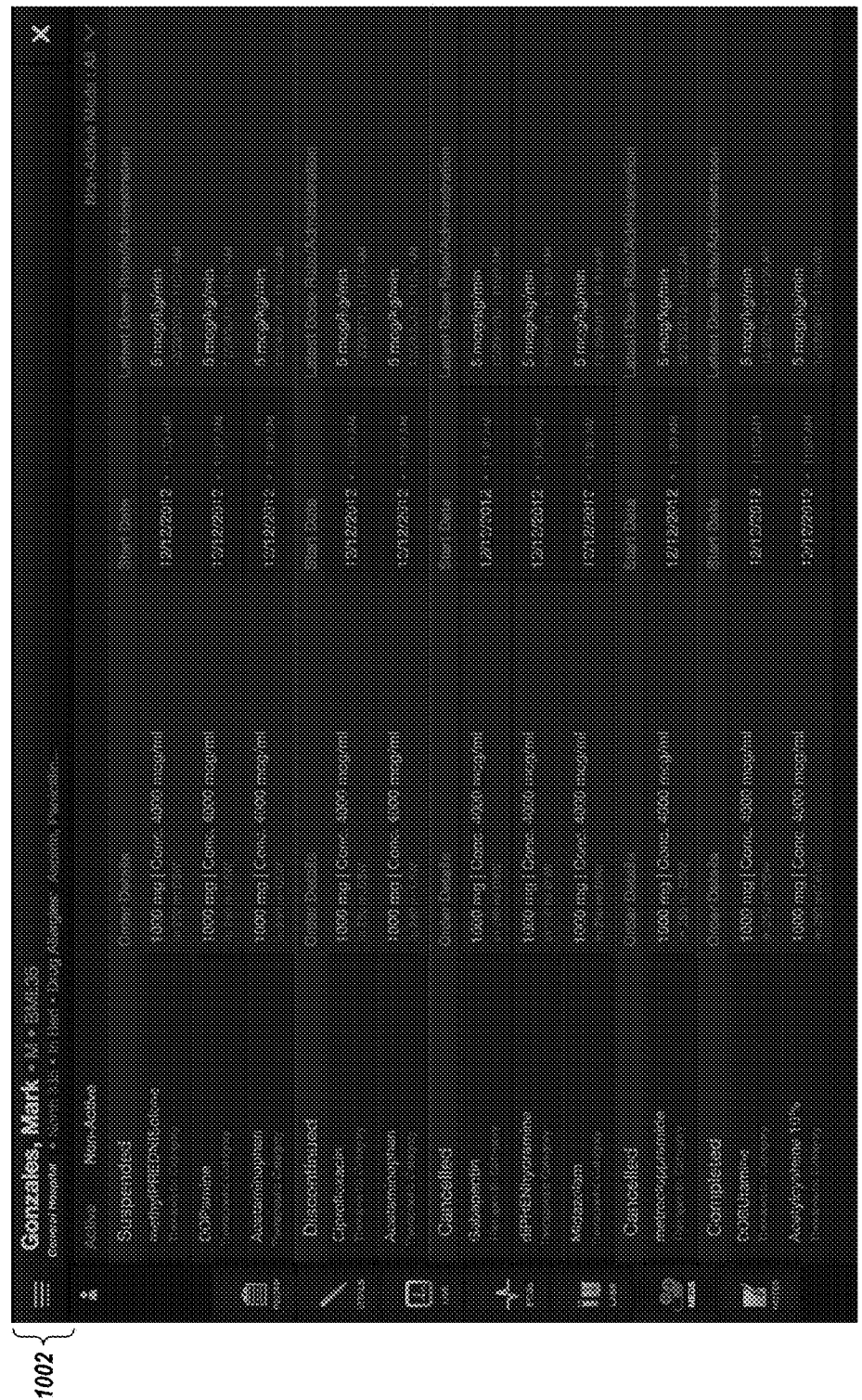

FIGS. 15A and 15B depicts an example medications ("meds") screen 1500. As discussed in further detail herein, the meds screen 1500 depicts active medications and/or non-active medications. In some examples, the meds screen 1500 is displayed in response to user selection of the meds icon 1016.

With particular reference to FIG. 15A, the meds screen 1500 displays active medications that have been ordered to be administered to the particular patient. In some examples, the medications can be grouped and displayed based on administration category. Example categories can include medications that are to be administered by continuous infusion "continuous infusions," medications that are to be administered on a schedule "scheduled," and medications that are to be administered pro re nata ("PRN") (as needed based on the circumstances). In the example of FIG. 15A, display regions 1504, 1506, 1508 are provided, each display region corresponding to a respective category of medication orders, and displaying medications for which there is an active order to the patient for each category. In some examples, medication information is provided for each medication. The medication information can include a name of the medication, a class of medication (e.g., a therapeutic class such as pain relief, anti-swelling, blood thinning, and the like), medication order details (e.g., dosage amounts, dosage concentrations, dosage intervals, and the like), start date (e.g., time/date administration of the medication began), latest dosage rate and time (e.g., for continuous infusion medications), and latest administration time/date (e.g., for scheduled and/or PRN medications).

In the example of FIG. 15A, the meds screen 1500 displays all active medications for the patient. In some examples, the meds screen 1500 is scrollable (e.g., upward/downward) to reveal additional medications. In some examples, active medication displayed in the meds screen

1500 can be filtered. For example, and in response to user input to an icon 1520, a drop-menu (not shown) can be displayed to enable the user to filter the active medications to show less than all.

In FIG. 15B, the meds screen 1500 displays similar information regarding medication as provided in FIG. 15A. The medications provided in FIG. 15B, however, are non-active medications. In some examples, non-active medications can include medications for which the order has been completed, suspended, discontinued and/or cancelled. In the meds screen of FIG. 15B, non-active medications can be grouped for display based on status (e.g., completed, suspended, discontinued and/or cancelled).

As similarly discussed above, the meds screen can be provided based on a template. In some examples, the template is user-specific and/or patient-specific. For example, in response to selection of the meds icon 1016 by the user, the DMS 160' determines the meds screen template to be used based on the user and/or the particular patient. In some examples, the user-specific and/or patient-specific template defines which medications and/or administration categories are to be displayed in the resultant meds screen. Based on the definition provided in the template, the DMS 160' can retrieve data from one or more corresponding data sources. In some examples, multiple data sources can be accessed, each data source corresponding to a facility that has or is administering medications to the patient. The DMS 160' can provide instructions to the mobile device to display the meds data/information as defined by the template.

Figure 16A:
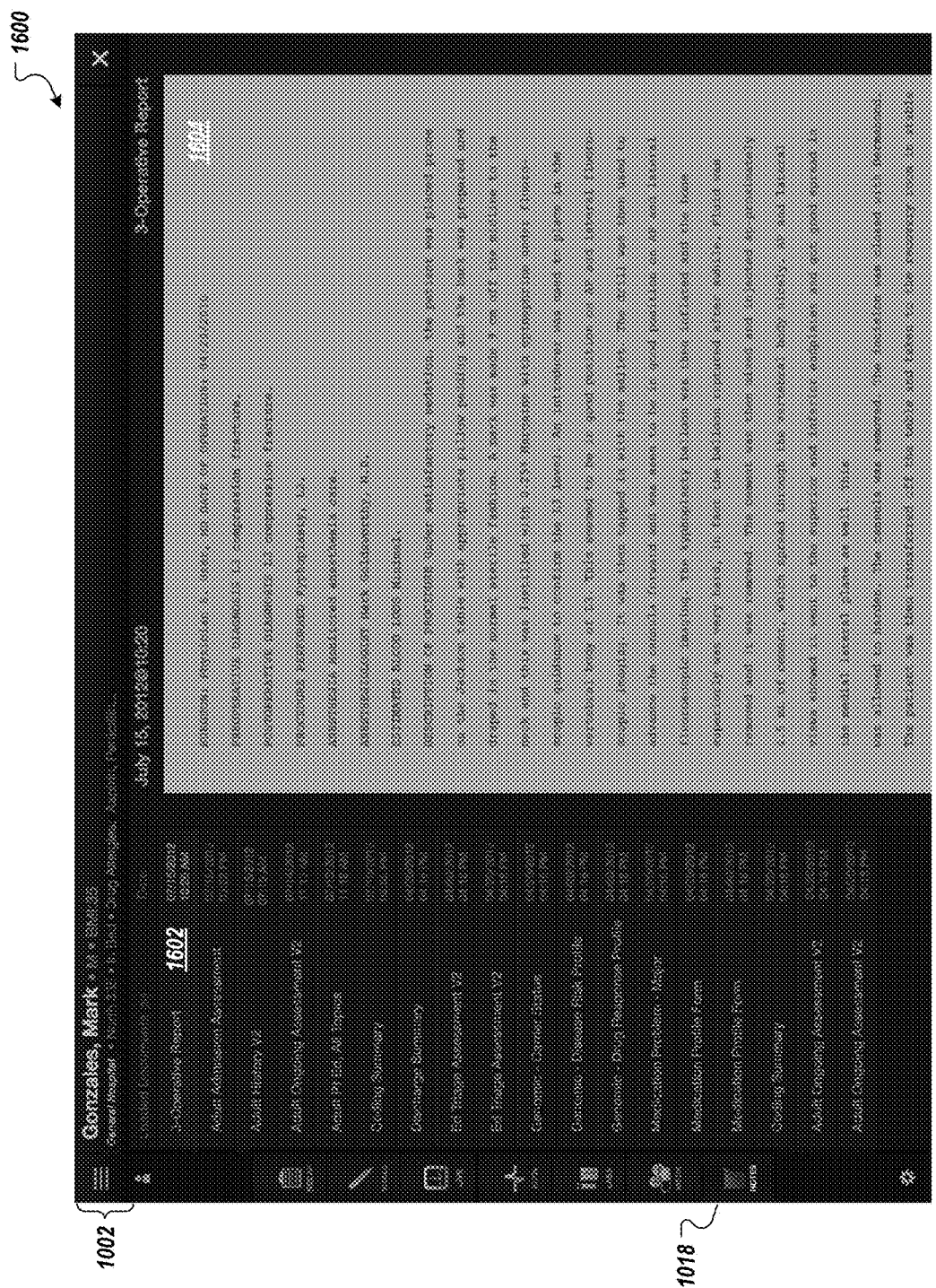
Figure 16B:
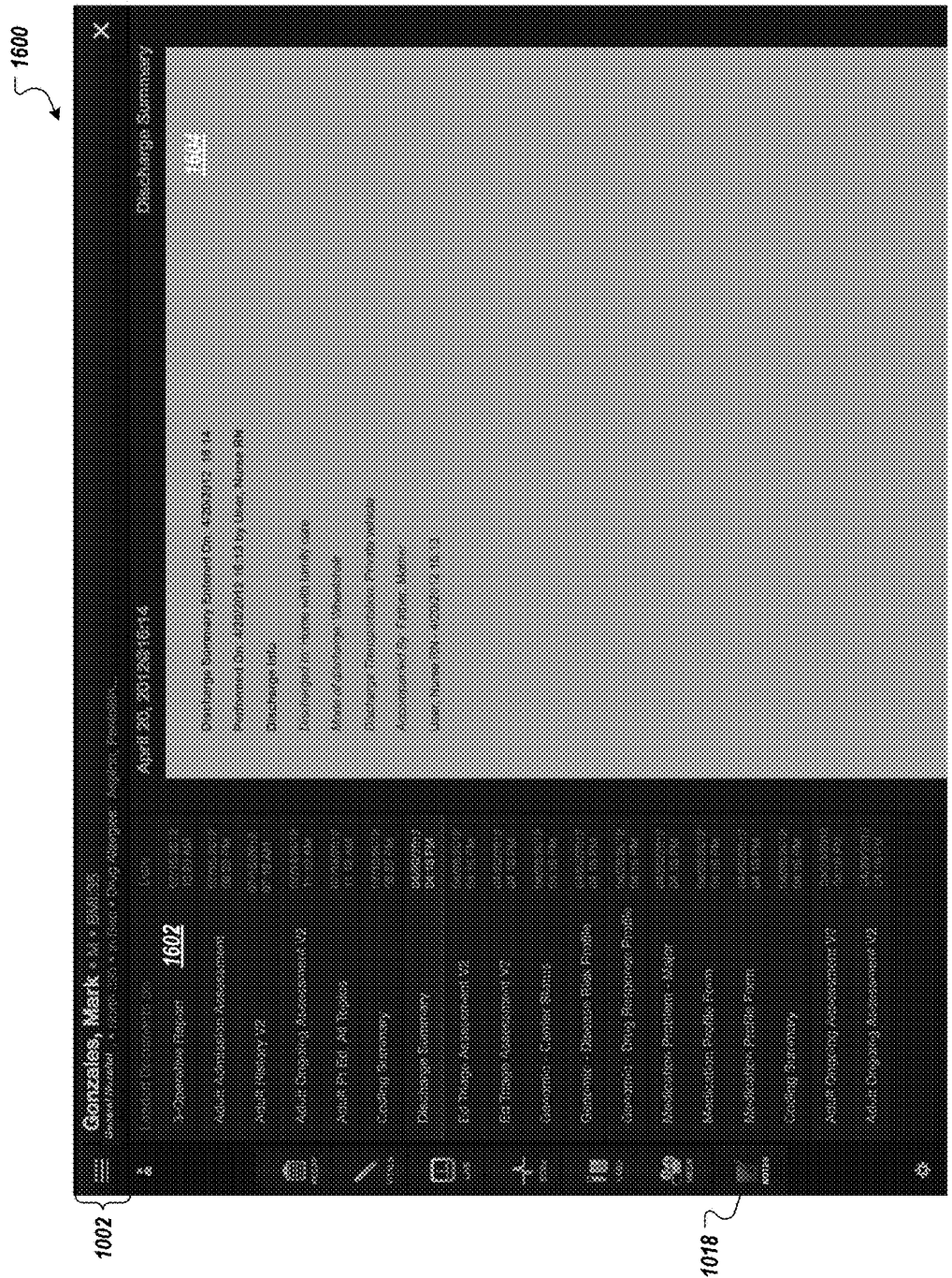

FIGS. 16A and 16B depict an example documents screen 1600. In some examples, the documents screen 1600 can be displayed in response to user selection of the notes icon 1018. In some examples, the documents screen 1600 provides a display region 1602 and a display region 1604. In some examples, the display region 1602 provides a menu of documents that are available for viewing on the mobile device. In some examples, the menu provides a type of the document and/or title of the document, as well as a date/time associated with the document (e.g., the date/time that the document was prepared, stored in a respective data source, last edited). Example documents can include a 3-Operative report, a patient medical history, a discharge summary, a medication profile and a coding summary. It is appreciated, however, that any appropriate document can be displayed on the mobile device. In some implementations, documents can include various text, digital image, and/or mixed content files. Example document files can include PDF, RTF, TXT, DOC, TIFF, BMP, JPEG, GIF and other appropriate document formats.

In some examples, a document is selected from the menu (in display region 1602) and, in response, the document is displayed in the display region 1604. In the example of FIG. 16A, the document "3-Operative Report" is selected from menu, and the corresponding document is displayed in the display region 1604. In the example of FIG. 16B, the document "Discharge Summary" is selected from menu, and the corresponding document is displayed in the display region 1604. In some examples, the document can be vertically and/or horizontally scrolled to reveal other parts of the document that are not visible in the display region 1604. In some examples, scrolling the document can be provided in response to a user swiping action on the touchscreen. In some implementations, the user can zoom in/out and/or change the font size of text within the displayed document. In some implementations, the user can edit any or some of the documents selected for display.

In some implementations, display of documents can be influenced based on rotation of the mobile device. In some examples, rotation of the mobile device from landscape to portrait can cause the menu (the display region 1602) to disappear and the document to appear in full screen. In some examples, rotation of the mobile device back to landscape can result in the menu (the display region 1602) to reappear and the document to be partially displayed. In some implementations, display behavior within any of the screens discussed herein (e.g., in FIGS. 7-16B) can be similarly influenced by rotation of the mobile device between landscape and portrait views.

As similarly discussed above, the documents screen can be provided based on a template. In some examples, the template is user-specific and/or patient-specific. For example, in response to selection of the notes icon 1018 by the user, a request is provided to the DMS 160', and the DMS 160' determines the documents screen template to be used based on the user and/or the particular patient. In some examples, the user-specific and/or patient-specific template defines which documents are to be displayed in the resultant documents screen. In some examples, the documents can include all documents that are available for the particular patient from one or more data sources. The DMS 160' can retrieve document data (e.g., document files) from one or more corresponding data sources. In some examples, multiple data sources can be accessed, each data source corresponding to a facility that has generated a document associated with the patient.

In some examples, the DMS 160' can provide instructions to the mobile device to display the menu defined by the template, including a summary of each available document (e.g., document type and/or title). In some examples, and in response to user selection of a document from the menu (e.g., in the display region 1602) a request can be provided to the DMS 160', requesting the particular document. In response, the DMS 160' can retrieve the document file from a corresponding data source and can provide the document file to the mobile device. The mobile device can process the document file to provide the document for display (e.g., in the display region 1604).

Figure 17:
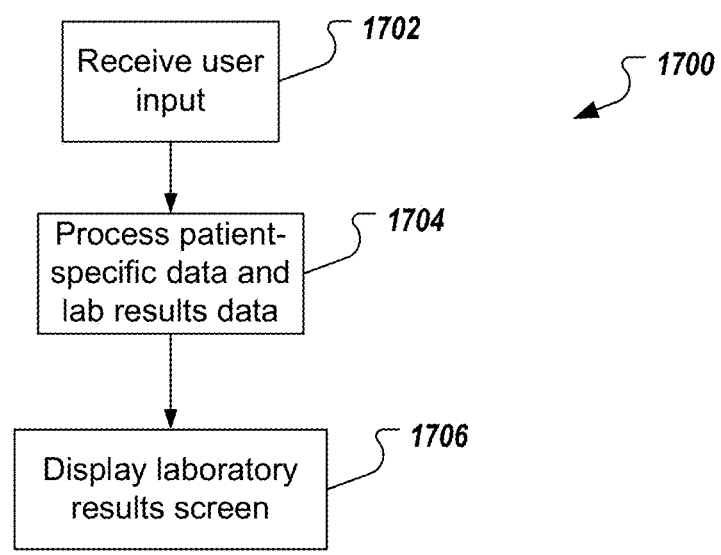
FIG. 17 is a flowchart illustrating an example process that can be executed device in accordance with implementations of the present disclosure.

FIG. 17 depicts an example process 1700 that can be executed in accordance with implementations of the present disclosure. In some examples, the example process 1700 can be provided in one or more computer-executable programs that can be executed using one or more computing devices (e.g., the mobile device 102 and/or the DMS 160, 160').

User input is received (1702). In some examples, the user input indicates a user command to display a laboratory results screen for a particular patient (e.g., the labs screen 1400 of FIG. 14A). Patient-specific data and lab results data are processed to provide one or more tables (1704). The laboratory results screen is displayed on the mobile device. In some examples, the laboratory results screen includes the one or more tables, each table of the one or more tables providing one or more discrete data values. In some examples, a discrete data value of the one or more discrete values is user-selectable to provide detailed result information (e.g., as discussed above with reference to FIGS. 14A and 14B).

Implementations of the present disclosure can be provided using digital electronic circuitry, or in computer hardware, firmware, software, or in combinations thereof. In some examples, implementations can be provided one or more computer program products, e.g., a computer program tangibly embodied in a machine-readable storage device, for execution by, or to control the operation of, data processing apparatus, and/or a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Such a computer program can include modules and/or code segments for executing one or more of the features, aspects and/or implementations provided herein.

Operations in accordance with implementations of the present disclosure can be performed by one or more programmable processors executing a computer program product to perform functions by operating on input data and generating output. By way of example, a computer program product can include modules and/or code segments corresponding to each of the method steps, aspects and/or features provided herein. Method steps can also be performed by, and apparatus of the present disclosure can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer can include a processor for executing instructions and one or more memory devices for storing instructions and data. Generally, a computer can also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks. The processor and the memory can be supplemented by, or incorporated in special purpose logic circuitry.

The present disclosure can be implemented in a system including, but not limited to the example systems described herein, which include a back-end component, e.g., as a data server, or that includes a middleware component, e.g., an application server, or that includes a front-end component, e.g., a client device, such as the mobile device 102, having a graphical user interface or a Web browser through which a user can interact with an implementation of the invention, or any combination of such back-end, middleware, or front-end components. The components of the system can be interconnected by any form or medium of digital data communication, e.g., a communication network.

A number of implementations have been described. Nevertheless, it will be understood that various modifications may be made without departing from the spirit and scope of the disclosure. For example, steps of the present disclosure can be performed in a different order and still achieve desirable results. Accordingly, other implementations are within the scope of the following claims.

The invention claimed is:

1. A computer-implemented method for providing a user of a mobile device access to patient information and patient physiological data, the method being executed using one or more processors and comprising:
    receiving, by the one or more processors, user input, the user input indicating a user command to display a laboratory results screen for a particular patient;
    determining, by the one or more processors, that the user command comprises a first request for first patient data stored within a first patient record module of a first facility system and a second request for second patient data stored within a second patient record module of a second facility system, the first patient data and the second patient data corresponding to the particular patient;
    processing, by a data management system, the first request for the first patient data and the second request for the second patient data to enable retrieval of the first patient data and the second patient data from the first facility system and the second facility system, respectively by using a user-facility index that maps an identifier associated with the user to the first facility system and the second facility system that the user is associated with as a healthcare provider, the data management system comprising a data cache module configured to selectively operate in a pass-through mode and a reposed mode;
    transmitting, by the data management system, the first request to a first host module of the first facility system, and the second request to a second host module of the second facility system, the first host module and the second host module respectively orchestrating processing of the first request and the second request received from the data management system;
    receiving, by the data management system, the first patient data from the first host module of the first facility system and the second patient data from the second host module of the second facility system, the first patient data having been at least partially translated in response to the first request, from a first vendor-specific vocabulary to a native language of the mobile device and the second patient data having been at least partially translated in response to the second request, from a second vendor-specific vocabulary to the native language of the mobile device, the second patient data comprising a format and a syntax different than the first patient data;
    providing, by the one or more processors, one or more tables comprising the first patient data and the second patient data, the first patient data and the second patient data being provided in an integrated and unified manner corresponding to the native language of the mobile device; and
    displaying the laboratory results screen on the mobile device by rendering graphics based on the first patient data and the second patient data provided in the integrated and unified manner and a user-specific template comprising a default template customized by the user, the laboratory results screen comprising the one or more tables, each table of the one or more tables providing one or more discrete data values, wherein a discrete data value of the one or more discrete values is user-selectable to provide detailed result information.

2. The method of claim 1, further comprising receiving, at the mobile device, the patient-specific data and the lab results data in response to the user input.

3. The method of claim 1, wherein the discrete data values are provided from the lab results data.

4. The method of claim 1, wherein the patient-specific data comprises patient physiological data recorded from the particular patient.

5. The method of claim 1, wherein the lab results data comprises lab results based on one or more samples taken from the particular patient.

6. The method of claim 1, wherein at least one discrete data value is color-coded.

7. The method of claim 6, wherein color-coding is based on a value range associated with a parameter represented by the at least one discrete data value.

8. The method of claim 7, wherein the discrete data value is color-coded based on a first color if the discrete data value is above the range, based on a second color if the discrete value is within the range, and based on a third color if the discrete value is below the range.

9. The method of claim 1, wherein at least one discrete data value is annotated.

10. The method of claim 9, wherein an annotation associated with the discrete data value indicates one of a decrease, a significant decrease, an increase and a significant increase in the discrete data value relative to another discrete data value.

11. The method of claim 9, wherein a warning annotation is associated with the discrete data value.

12. The method of claim 1, further comprising receiving a user-selection associated with a discrete data value and, in response, displaying a window, the window displaying detailed information associated with the discrete data value.

13. The method of claim 12, where the detailed information comprises at least one of a name of a laboratory that generated the discrete data value, collection information associated with collection of a specimen of the particular patient, textual comments, and laboratory contact information.

14. A non-transitory computer-readable storage device coupled to one or more processors and having instructions stored thereon which, when executed by the one or more processors, cause the one or more processors to perform operations for providing a user of a mobile device access to patient information and patient physiological data, the operations comprising:
receiving, by the one or more processors, user input, the user input indicating a user command to display a laboratory results screen for a particular patient;
determining, by the one or more processors, that the user command comprises a first request for first patient data stored within a first patient record module of a first facility system and a second request for second patient data stored within a second patient record module of a second facility system, the first patient data and the second patient data corresponding to the particular patient;
processing, by a data management system, the first request for the first patient data and the second request for the second patient data to enable retrieval of the first patient data and the second patient data from the first facility system and the second facility system, respectively by using a user-facility index that maps an identifier associated with the user to the first facility system and the second facility system that the user is associated with as a healthcare provider, the data management system comprising a data cache module configured to selectively operate in a pass-through mode and a reposed mode;
transmitting, by the data management system, the first request to a first host module of the first facility system, and the second request to a second host module of the second facility system, the first host module and the second host module respectively orchestrating processing of the first request and the second request received from the data management system;
receiving, by the data management system, the first patient data from the first host module of the first facility system and the second patient data from the second host module of the second facility system, the first patient data having been at least partially translated in response to the first request, from a first vendor-specific vocabulary to a native language of the mobile device and the second patient data having been at least partially translated in response to the second request, from a second vendor-specific vocabulary to the native language of the mobile device, the second patient data comprising a format and a syntax different than the first patient data;
providing, by the one or more processors, one or more tables comprising the first patient data and the second patient data, the first patient data and the second patient data being provided in an integrated and unified manner corresponding to the native language of the mobile device; and
displaying the laboratory results screen on the mobile device by rendering graphics based on the first patient data and the second patient data provided in the integrated and unified manner and a user-specific template comprising a default template customized by the user, the laboratory results screen comprising the one or more tables, each table of the one or more tables providing one or more discrete data values, wherein a discrete data value of the one or more discrete values is user-selectable to provide detailed result information.

15. A system, comprising:
one or more processors; and
a computer-readable storage medium in communication with the one or more processors and having instructions stored thereon which, when executed by the one or more processors, cause the one or more processors to perform operations for providing a user of a mobile device access to patient information and patient physiological data, the operations comprising:
receiving, by the one or more processors, user input, the user input indicating a user command to display a laboratory results screen for a particular patient;
determining, by the one or more processors, that the user command comprises a first request for first patient data stored within a first patient record module of a first facility system and a second request for second patient data stored within a second patient record module of a second facility system, the first patient data and the second patient data corresponding to the particular patient;
processing, by a data management system, the first request for the first patient data and the second request for the second patient data to enable retrieval of the first patient data and the second patient data from the first facility system and the second facility system, respectively by using a user-facility index that maps an identifier associated with the user to the first facility system and the second facility system that the user is associated with as a healthcare provider, the data management system comprising a data cache module configured to selectively operate in a pass-through mode and a reposed mode;

transmitting, by the data management system, the first request to a first host module of the first facility system, and the second request to a second host module of the second facility system, the first host module and the second host module respectively orchestrating processing of the first request and the second request received from the data management system;

receiving, by the data management system, the first patient data from the first host module of the first facility system and the second patient data from the second host module of the second facility system, the first patient data having been at least partially translated in response to the first request, from a first vendor-specific vocabulary to a native language of the mobile device and the second patient data having been at least partially translated in response to the second request, from a second vendor-specific vocabulary to the native language of the mobile device, the second patient data comprising a format and a syntax different than the first patient data;

providing, by the one or more processors, one or more tables comprising the first patient data and the second patient data, the first patient data and the second patient data being provided in an integrated and unified manner corresponding to the native language of the mobile device; and displaying the laboratory results screen on the mobile device by rendering graphics based on the first patient data and the second patient data provided in the integrated and unified manner and a user-specific template comprising a default template customized by the user, the laboratory results screen comprising the one or more tables, each table of the one or more tables providing one or more discrete data values, wherein a discrete data value of the one or more discrete values is user-selectable to provide detailed result information.

* * * * *